(12) United States Patent
Lassila

(10) Patent No.: US 12,208,132 B2
(45) Date of Patent: *Jan. 28, 2025

(54) THERAPEUTIC APAC MOLECULE COMPRISING HEPARIN CONJUGATED TO A PLASMA PROTEIN

(71) Applicant: APLAGON OY, Helsinki (FI)

(72) Inventor: Riitta Lassila, Helsinki (FI)

(73) Assignee: Aplagon Oy, Helsinki (FI)

( * ) Notice: Subject to any disclaimer, the term of this patent is extended or adjusted under 35 U.S.C. 154(b) by 153 days.

This patent is subject to a terminal disclaimer.

(21) Appl. No.: 17/855,932

(22) Filed: Jul. 1, 2022

(65) Prior Publication Data

US 2022/0339264 A1 Oct. 27, 2022

Related U.S. Application Data

(62) Division of application No. 15/505,366, filed as application No. PCT/EP2015/069327 on Aug. 24, 2015, now Pat. No. 11,446,361.

(30) Foreign Application Priority Data

Aug. 26, 2014 (GB) ..................................... 1415062
Jun. 17, 2015 (GB) ..................................... 1510637

(51) Int. Cl.
*A61K 47/61* (2017.01)
*A61K 38/38* (2006.01)
*A61K 47/64* (2017.01)

(52) U.S. Cl.
CPC ............ *A61K 38/385* (2013.01); *A61K 47/61* (2017.08); *A61K 47/64* (2017.08); *A61K 47/643* (2017.08)

(58) Field of Classification Search
CPC .... A61K 38/385; A61K 47/61; A61K 47/643; A61K 47/64
See application file for complete search history.

(56) References Cited

U.S. PATENT DOCUMENTS 5,009,888 A * 4/1991 Dunn ................... A61K 39/395
424/94.63
2012/0270299 A1* 10/2012 Blaney ................. C12N 9/6459
435/264

FOREIGN PATENT DOCUMENTS

WO    WO-9926983 A1 * 6/1999 ........... A61K 31/726

OTHER PUBLICATIONS

Hogrefe Dissertation 2005 (Year: 2005).*
Huang et al 2004 (Year: 2004).*

* cited by examiner

*Primary Examiner* — Catherine S Hibbert
(74) *Attorney, Agent, or Firm* — Patrick M. Torre; Stites & Harbison PLLC

(57) ABSTRACT

The invention relates to an anti-thrombotic molecule having both antiplatelet and anticoagulant (APAC) activity; its use as a medicament; its selective configuration and use as an anticoagulant and platelet inhibitor, or its selective configuration and use predominantly as either an anticoagulant or a platelet inhibitor; and a method for its production.

6 Claims, 19 Drawing Sheets

Heparin concentration at 10 μg/mL

Heparin concentration at 30 μg/mL

THERAPEUTIC APAC MOLECULE COMPRISING HEPARIN CONJUGATED TO A PLASMA PROTEIN

This is a divisional patent application claiming priority from U.S. utility patent application Ser. No. 15/505,366 filed on Feb. 21, 2017, which in turn is the national stage of international patent application no. PCT/EP2015/069327 filed on Aug. 24, 2015, which in turn claims priority from British Patent Applications Ser. No. 1415062.7 filed on Aug. 26, 2014 and Ser. No. 1510637.0 filed on Jun. 17, 2015, the disclosures of which are incorporated herein by reference in their entirety.

TECHNICAL FIELD

The invention relates to an anti-thrombotic molecule having both anti-platelet and anti-coagulant (APAC) activity; its use as a medicament; its selective configuration and use as an anti-coagulant and platelet inhibitor, or its selective configuration and use, predominantly, as either an anti-coagulant or a platelet inhibitor; and a method for its production. The invention has use in both the medical and veterinary industries.

BACKGROUND

This physiological process of coagulation, during which the circulating blood turns from a liquid into a gel-like matrix, is complex and involves multiple biochemical reactions that progress sequentially.

The physiological process of clotting involves vascular-injury specific activation, adhesion, and aggregation of platelets, to create a primary plug or seal, followed by the deposition and maturation of fibrin to create a stable clot. The former platelet activity can be inhibited by platelet inhibitors and the latter fibrin deposition can be inhibited by anti-coagulants.

The clotting process begins almost instantly after injury to a blood vessel damages the endothelium lining and/or deeper layers of the vessel. Exposure of blood to the space under the endothelium initiates two processes: changes in platelets, and the exposure of sub-endothelial tissue factor to plasma coagulation factor VII, which among other coagulation factors significantly contributes to thrombin generation and fibrin formation.

When the endothelium is damaged the underlying collagen is exposed to circulating platelets, which bind directly to collagen via collagen-specific glycoprotein surface receptors. Indirectly, von Willebrand factor tethers platelets into close contact with collagen and also bridges platelets with collagen. Localization of platelets to the extracellular matrix promotes collagen interaction with platelet glycoprotein VI triggering a signaling cascade that results in activation of platelet integrins and causes the subsequent adherence of the platelets to the site of injury. This results in an immediate platelet-formed plug at the site of injury; termed primary haemostasis.

Secondary haemostasis occurs simultaneously and involves the so-called 'coagulation cascade'. Additional coagulation factors or clotting factors, beyond factor VII, respond in a complex cascade resulting in the enzymatic cleavage of fibrinogen to form fibrin strands which strengthen the platelet plug. The coagulation cascade consists of a series of steps in which a protease cleaves and subsequently activates a zymogen which then acts as the next protease in the sequence. The conclusion of these reactions is the conversion of fibrinogen, a soluble protein, into insoluble threads of fibrin on activated platelet surfaces. Together with contracting platelets, the fibrin threads form a stable blood clot. The critical von Willebrand factor and fibrinogen are provided by platelets as well as in addition to plasma.

The coagulation cascade is classically (and somewhat artificially) divided into three pathways; firstly the tissue factor and secondly the contact activation pathways, which both activate the third "final common pathway" of factor X and thrombin leading to fibrin formation. The main role of the tissue factor pathway is to generate a "thrombin burst", a process by which thrombin, the most important constituent of the coagulation cascade in terms of its feedback activation roles, is formed very rapidly. Interestingly, thrombin is the link between platelet activation and coagulation because, whilst produced by the coagulation cascade, it is the most potent platelet activator, thus therapeutics that can target this molecule are likely to be extremely effective anti-thrombotics.

The coagulation cascade is a normal physiological process which aims at preventing significant blood loss or haemorrhage following vascular injury. Eventually, blood clots are reorganised and resorbed by a process termed fibrinolysis. The main enzyme responsible for this process (plasmin) is regulated by various activators and inhibitors. Further, the coagulation system overlaps with the immune and complement system, so as to physically trap invading microbes in blood clots, increase vascular permeability and provide chemotactic agents for phagocytic cells. In addition, some of the products of the coagulation system are directly antimicrobial.

There are times, however, when a blood clot (also known as a thrombus) will form when it is not needed. For instance, some high risk conditions such as acute medical illness, prolonged immobilization, surgery, or cancer can increase the risk of developing a blood clot. Moreover, physiological problems with the coagulation process may pre-dispose an individual to haemorrhage, thrombosis, and occasionally both, which can have significant consequences in association with atherosclerotic cardiovascular disease and/or cardiac arrhythmias.

Anti-platelet agents and anti-coagulants are used to treat clotting disorders. Anti-platelet agents include aspirin, dipyridamole, ticlopidine, clopidogrel, ticagrelor and prasugrel; the parenteral glycoprotein IIb/IIIa inhibitors are used during coronary interventions (angioplasty and stenting). Of the anti-coagulants, warfarin (and related coumarins) and heparin are the most commonly used, but direct oral anti-coagulants also include thrombin inhibitor dabigatran and inhibitors of activated factor X, such as rivaroxaban, apixaban and edoxaban.

Antithrombin (AT) is a serine protease inhibitor and one of the major plasma inhibitors of the coagulation proteases. AT blocks/regulates the coagulation cascade by, for example, inhibiting thrombin (factor IIa) and activated factor X (factor Xa). Interaction of AT with these factors is increased by the presence of heparin (unfractionated heparin; UFH) and low molecular weight heparins (LMWHs; fractionated heparin), which inhibit the coagulation process through binding to AT via a specific penta-saccharide sequence. This binding leads to a conformational change of AT, which accelerates its inhibition of factors IIa, Xa, and other proteases involved in blood clotting. Once dissociated, heparin and LMWH are free to bind to other AT molecules and subsequently inhibit more thrombin and factor Xa.

In addition to AT there are other naturally occurring anticoagulants, of which protein C and S, tissue factor pathway inhibitor and heparin cofactor II play an important role. The activity of these molecules is also enhanced by heparins.

Primarily, standard heparin preparations are used for the systemic treatment of thrombosis. They are most efficient in platelet-poor thrombi, such as venous thrombi, where coagulation activity prevails. The clinically used standard heparins, though effective in the systemic treatment of thrombosis by blocking the further growth of thrombosis, are not effective enough alone to prevent platelet-driven thrombotic complications in arteries, associated with endogenous rupture of an atheromatous plaque or exogenous angioplasty or vascular or microvascular surgery.

Arterial interventions, such as angioplasty [PT(C)A=percutaneous transluminal (coronary) angioplasty] with or without stenting and vascular or microvascular surgery, as well as (directional) arterectomy and peripheral or pulmonary thrombendarterectomy, represent a growing modality of treatment for cardiovascular diseases. Accordingly, platelet-driven arterial thrombosis, which occurs in connection with endogenous vascular or microvascular injuries and/or exogenous interventions such as insertion and maintenance of arterio-venous fistula or arterio-venous grafts, is a frequently encountered problem and in these situations the traditional systemic anti-coagulation treatment of thrombosis is often of limited efficacy.

Current systemic anti-thrombotic treatment in connection with arterial interventions include the combination of an anti-coagulant, such as UFH (on average 15 kDa) or LMWHs (on average 7.5 kDa), with an anti-platelet drug, such as acetylsalicylic acid (cyclooxygenase inhibitor), clopidogrel or other ADP antagonists. Other developments are also represented by potent platelet glycoprotein IIb/IIIa, von Willebrand factor and fibrinogen receptor antagonists, such as abciximab, tirofiban and eptifibatide. These relatively new intravenously administered combination treatments have succeeded in preventing 30-35% of acute thrombotic closures of the interventionally treated thrombus-prone vessels. The earliest inpatient bleeding risk (major bleeding) requiring infusion of blood products is around 6-7%, and with the use of potent platelet ADP receptor blockers major bleeds increase to 12-15% in outpatient setting during the first month. The associated risk for mortality is 15-30-fold in case of spontaneous bleeds during the first month of follow-up.

Unfortunately, systemic treatment with unfractionated heparin has disadvantages, such as unpredictable bioavailability, a short half-life, non-specific binding to proteins leading to compromised antithrombin/AT function and immunogenic effects which, with platelet factor 4 (PF4), leads to thrombocytopenia and thrombosis. These unwanted effects have been mitigated by the use of the low-molecular-weight fractionated heparins which, unfortunately, have also limited efficacy against arterial thrombosis due to a limited effect on fibrin-bound thrombin, and on platelet-bound factor Xa, and due to the partial neutralization of heparin-activity by platelet-secreted PF4. Thus, there is a great need for the development of an effective and reliable and safe therapeutic to prevent and/or treat thromboses associated with vascular or microvascular injuries and interventions.

We have previously found (WO9926983) that a synthetic molecule comprising large chain (75±25 KDa) native heparin proteoglycans (HEP-PG), obtainable from mammalian mast cells, when attached to a protein core expresses potent antithrombotic properties, which are based on its capacity to inhibit platelet-collagen interactions via a strong inhibition of platelet activation triggered by platelet adhesion to collagen. This molecule is therefore effective as an anti-platelet treatment and is most suitable for local application and is ideally used in combination with a systemic anti-platelet drug. Advantageously, this molecule at least when locally administered preserves systemic platelet function which ensures normal haemostatic responses.

Other researchers (U.S. Pat. No. 5,529,986) have made a synthetic antithrombotic molecule comprising the attachment of unfractionated heparin chains (about 20-100 chains) to a straight-chain polyamide, such as a polylysine. This molecule has a different mechanism of action compared to that described in WO9926983 above as it binds antithrombin and enhances its activity. Thus, this molecule is efficacious as an anti-coagulant.

Our ongoing research has led us to develop a further class of synthetic anti-thrombotic molecules based upon the use of heparin. However, we have surprisingly found that our new class of molecules has, advantageously, both anti-platelet activity and anti-coagulant activity. To our knowledge, this is the first time such dual molecules have been identified. Moreover, we have discovered that the propensity of our novel class of molecules to act, predominantly or to a larger extent, in an anti-platelet or anti-coagulant fashion can be manipulated/designed having regard to the amount of heparin attached to, or included in, each molecule. Finally, we have also discovered that our novel class of molecules have, advantageously, local action and so can be used in a targeted fashion without concerns about systemic effects.

SUMMARY

According to a first aspect of the invention there is provided an anti-thrombotic molecule having both anti-platelet and anti-coagulant (APAC) activity comprising a plasma protein to which there is attached, via a plurality of linker molecules, a plurality of heparin chains each chain having a MW between 10-21 KDa and further wherein the number of said heparin chains attached to said plasma protein is selected from the group comprising 4, 5, 6, 7, 8, 9, 10, 11, 12, 13, 14, 15, and 16.

Reference herein to the number of heparin chains attached to said plasma protein is determined having regard to a colorimetric Sulphated glycosaminoglycan assay, Blyscan Assay Kit (e.g. Biocolor Ltd., UK) using a heparin standard at specified concentrations to provide a calibration curve against which test samples can be read/determined. Thus, the number of heparin chains referred to in the main statement of invention is correlated with column 1 of Table I. The particular assay used is described herein.

The antiplatelet (AP) and anticoagulant (AC) activity is unique and extremely advantageous because it enables the molecules to address instances where an antiplatelet activity is needed and/or an anticoagulant activity is needed such as in curved vessels or in stenotic vessels where at the site of stenosis AP is needed, and distally as well as proximally when there is turbulence and a thrombus growth is mediated by thrombin an AC action is needed.

In addition to the favourable dual functionality, we have also discovered that the molecules of the invention have a strong binding capacity to extracellular matrix, including collagen and von Willebrand factor, and therefore they have targeted local anti-thrombotic action. This is a highly desirable feature as it means the molecules can be used at a specific site to treat a specific condition without the concern that they may have deleterious systemic anti-thrombotic effects that may potentially give rise to bleeding or hemorrhaging. This advantageous targeting exists regardless of the mode of administration i.e. locally or systemically.

Reference herein to targeted anti-thrombotic action refers to retention of the molecules of the invention at the site of application for significant periods of time for example longer than 24 hours, and moreover, ideally, longer than 48 hours or 50 hours and even up to 120 hours. Notably, this retention at the site of application occurs both when administered outside and inside the blood vessel.

In a preferred embodiment of the invention said plasma protein is an albumin, globulin or fibrinogen, ideally it is serum albumin or alpha2-macroglobulin and more ideally human serum albumin (HSA) or human alpha2-macroglobulin. As is known generally, serum albumin is produced by the liver, is dissolved in blood plasma and is the most abundant blood protein in mammals. Serum albumin is a globular, water-soluble protein of approximate molecular weight of 66,000 Daltons. As is also known alpha2-macroglobulin (α2M and A2M) is a large plasma protein, in fact it is the largest major non-immunoglobulin protein in plasma and is produced mainly by the liver. Alpha2-macroglobulin acts as an anti-protease and is able to inactivate a large variety of proteinases.

In yet a further preferred embodiment of the invention said plasma protein is recombinant.

In yet a further preferred embodiment of the invention said heparin is unfractionated heparin. More ideally still said heparin is of mammalian origin, ideally, human or porcine. In the instance where the plasma protein is human and the heparin porcine or bovine heparin said APAC molecule represents a chimeric molecule.

Preferably, the heparin has a MW selected from the group comprising: 10, 11, 12, 13, 14, 15, 16, 17, 18, 19, 20 or 21 KDa, ideally 15 or 16 or 17 KDa.

In yet a further preferred embodiment of the invention said heparin is recombinant.

In yet a more preferred embodiment of the invention said linker molecule, at least when linkage of said heparin to said plasma protein is complete, is a single linker molecule that binds one molecule of heparin therefore the attachment of one linker molecule to said plasma protein results in the attachment of one molecule of heparin to said plasma protein. Thus, the stoichiometry of said linker to said heparin is 1:1. Preferably said linker is an amine linker and so links with amino groups on said heparin and plasma protein, ideally, but not exclusively, said linker conjugates with serine on the heparin chain, ideally located at the end or near the end of said chain, and ideally, but not exclusively, lysine on the plasma protein. More ideally yet said linker conjugates said heparin and plasma protein by the use of disulfide bridges. Yet more preferably said linker is a hetero-bi-functional cross-linker such as a SPDP linker or a homo-bi-functional cross-linker such as a DTSP linker.

SPDP (available commercially from for example from Sigma-Aldrich or Thermo Scientific Pierce) is a short-chain cross-linker used for amine-to-sulfhydryl conjugation via N-hydroxysuccinimide (NHS)-ester and pyridyldithiol reactive groups, and it forms cleavable (reducible) disulfide bonds with cysteine sulfhydryls. It is available in short chain and long chain versions. The long chain version is available in a sulfonated form and is water-soluble. We prefer to use 3-(2-Pyridyldithio)propionic acid N-hydroxysuccinimide ester. Although all the SPDPs contain an amine-reactive N-hydroxysuccinimide (NHS) ester that will react with lysine residues to form a stable amide bond and, at the other end of the linker, there is a pyridyl disulfide group that will react with sulfhydryls to form a reversible disulfide bond.

DTSP (3,3'-Dithiodipropionicacid di(N-hydroxysuccinimide (NHS)-ester), available commercially from, for example, Sigma-Aldrich or Thermo Scientific Pierce) is a short-chain cross-linker used for amine-to-amine conjugation via N-hydroxysuccinimide (NHS) ester groups. It is available in short chain and long chain versions. The long chain version is available in a sulfonated form (N-hydroxysulfosuccinimide (sulfo-NHS) ester) and is water-soluble. DTSPs contain two amine-reactive N-hydroxysuccinimide (NHS) ester groups and a disulfide bridge in the spacer arm. N-hydroxysuccinimide ester reacts with primary amine containing residues to form stable amide bonds with a cleavable disulfide bond in the linker molecule.

Accordingly, the generic formulae for our preferred synthetic molecule can be written as follows:

(Hep-linker)$n$-PlPr where n=4-16;
PlPr is a plasma protein such as human serum albumin or human alpha2-macroglobulin; and Heparin chain is 10-21 KDa More particularly, where we use our preferred linker 3-(2-Pyridyldithio)propionic acid N-hydroxysuccinimide ester (SPDP) or (3,3'-Dithiodipropionicacid di(N-hydroxysuccinimide ester) (DTSP), our preferred synthetic molecule can be written as follows:

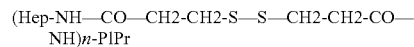

(Hep-NH—CO—CH2-CH2-S—S—CH2-CH2-CO—NH)$n$-PlPr where n=4-16;
PlPr is a plasma protein such as human serum albumin or human alpha2-macroglobulin; and Heparin chain is 10-21 KDa Whilst it is possible to attach up to 36 chains of heparin to each plasma protein such as albumin, specifically HSA, we have discovered that the attachment of between 4-16 heparin chains to each plasma protein provides the desirable dual functionality of both antiplatelet activity and anticoagulant activity. Moreover, as the data herein show, we have also discovered that the attachment of less than 6 heparin chains, ideally between 4-6 heparin chains, to each plasma protein provides predominantly, or to a larger extent, the desirable anticoagulant activity whereas the attachment of more than 8 heparin chains, ideally between 8-16 heparin chains, to each plasma protein provides predominantly, or to a larger extent, the desirable antiplatelet activity.

Accordingly in yet a further preferred embodiment of the invention said APAC molecule has 6 or less, such as between 4-6, heparin chains attached to said plasma protein when said molecule is to be used predominantly, or to a larger extent, as an anti-coagulant.

Accordingly in yet a further preferred embodiment of the invention said APAC molecule has 8 or more, such as between 8-16, heparin chains attached to said plasma protein when said molecule is to be used predominantly, or to a larger extent, as an antiplatelet/platelet inhibitor.

Accordingly in yet a further preferred embodiment of the invention said APAC molecule has 8 heparin chains attached to said plasma protein when said molecule is to be used predominantly, or to a larger extent, as an anti-platelet/platelet inhibitor.

Accordingly in yet a further preferred embodiment of the invention said APAC molecule has 11 heparin chains attached to said plasma protein when said molecule is to be used predominantly, or to a larger extent, as an anti-platelet/platelet inhibitor.

Thus, the preferentially linking of a certain number of heparin chains to each plasma protein core can influence the predominant function of the synthetic molecule. This remarkable feature has technical application because, whilst the result to be achieved when using our molecule(s) is anti-thrombotic, there are instances where emphasis on an antiplatelet activity is required and other instances where additional emphasis on an anticoagulant activity is required. For example, where one is treating vessels such as veins where shear rate is relatively low, i.e. larger vessel lumen and lower blood flow rate, an anti-thrombotic with a predominance on, or emphasis on, anti-coagulation is highly desirable. Whereas, where one is treating vessels such as arteries or an arterio-venous fistula, for example, where shear rate is relatively high i.e. a higher blood flow rate or vessels with a smaller vessel lumen and so where blood flow rate is high, an anti-thrombotic with a predominance on, or emphasis on, antiplatelet activity is highly desirable. Similarly, where implants such as catheters, stents or devices used to perform balloon angioplasty are used they can be coated with the APAC molecules of the invention and the type of APAC molecules used, ideally, will be determined having regard to the nature of the vessel into which the implants are to be inserted.

According to a second aspect of the invention there is provided an anti-thrombotic molecule having both antiplatelet and anticoagulant (APAC) activity comprising a plasma protein to which there is attached, via a plurality of linker molecules, a plurality of heparin chains each having a MW between 10-21 KDa and further wherein the number of said heparin chains attached to said plasma protein is selected from the group comprising 4, 5, 6, 7, 8, 9, 10, 11, 12, 13, 14, 15, and 16 for use as a medicament.

According to a third aspect of the invention there is provided an anti-thrombotic molecule having both antiplatelet and anticoagulant (APAC) activity comprising a plasma protein to which there is attached, via a plurality of linker molecules, a plurality of heparin chains each having a MW between 10-21 KDa and further wherein the number of said heparin chains attached to said plasma protein is selected from the group comprising 4, 5, 6, 7, 8, 9, 10, 11, 12, 13, 14, 15, and 16 for use as an anti-thrombotic.

In a preferred embodiment of this aspect of the invention said anti-thrombotic is locally acting. By this we mean the anti-thrombotic binds to the extracellular matrix and therefore it is retained at the site of application, or at the site of intended action, with prolonged local activity. Indeed, this locally acting activity is advantageous as it means the molecules of the invention are effectively targeted to the site where they are most needed, i.e. where a thrombosis is likely to occur, in other words, the extracellular matrix where both collagen and von Willebrand factor are present/integral components.

According to a fourth aspect of the invention there is provided the use of an anti-thrombotic molecule having both antiplatelet and anticoagulant (APAC) activity comprising a plasma protein to which there is attached, via a plurality of linker molecules, a plurality of heparin chains each having a MW between 10-21 KDa and further wherein the number of said heparin chains attached to said plasma protein is selected from the group comprising 4, 5, 6, 7, 8, 9, 10, 11, 12, 13, 14, 15, and 16 for use in the manufacture of a medicament for treating a thrombosis or a suspected thrombosis.

Reference herein to a suspected thrombosis refers to any instance, circumstance or condition that may give rise to a thrombosis, such as (without limitation) the performance of a surgical intervention e.g. surgical thrombectomy, in this example the molecules of the invention could be administered to the operative site or infused into the vessel that has been operated upon or infused into a neighboring downstream vessel whose blood supply will flow by/to said operative site.

In a preferred embodiment of this aspect of the invention said medicament is an anti-thrombotic, ideally locally acting. By locally acting we mean that the anti-thrombotic binds to the extracellular matrix and therefore it is retained at the site of application with prolonged local activity. Indeed, this locally acting activity is advantageous as it means the molecules of the invention are effectively targeted to the site where they are most needed i.e. where a thrombosis is likely to occur, in other words, the extracellular matrix where both collagen and von Willebrand factor are present/integral components.

In the afore aspects of the invention preferably said APAC molecule has 6 or less, such as between 4-6, heparin chains attached to said plasma protein, via said linkers, when said molecule is to be used predominantly, or to a larger extent, as an anti-coagulant.

Similarly, in the afore aspects of the invention preferably said APAC molecule has 8 or more, such as between 8-16, heparin chains attached to said plasma protein, via said linkers, when said molecule is to be used predominantly, or to a larger extent, as an anti-platelet/platelet inhibitor.

In yet further preferred embodiments of the invention said APAC molecules can be used in the treatment or prevention of thrombotic complications, such as those associated with endogenous rupture of an atheromatous plaque; or after thrombolytic therapy to prevent re-occlusion; or exogenous angioplasty; or vascular or microvascular surgery; arterial interventions such as angioplasty, in particular, percutaneous transluminal (coronary) angioplasty with or without stenting; (directional) arterectomy; peripheral or pulmonary thrombendarterectomy; platelet-driven arterial thrombosis; vascular or microvascular injuries; thrombotic thrombocytopenic purpura or exogenous interventions, such as insertion and maintenance of arterio-venous fistula or arterio-venous grafts and Antithrombin (AT) deficiency.

According to a fifth aspect of the invention there is provided the use of an anti-thrombotic molecule having both antiplatelet and anticoagulant (APAC) activity comprising a plasma protein to which there is attached, via a plurality of linker molecules, a plurality of heparin chains each having a MW between 10-21 KDa and further wherein the number of said heparin chains attached to said plasma protein is selected from the group comprising 4, 5, 6, 7, 8, 9, 10, 11, 12, 13, 14, 15, and 16 for use in treating Ischemia reperfusion injury or acute kidney injury or myocardial infarction or stroke or peripheral arterial occlusive disease or mesenterial ischemia.

Alternatively, according to a sixth aspect of the invention there is provided the use of an anti-thrombotic molecule having both antiplatelet and anticoagulant (APAC) activity comprising a plasma protein to which there is attached, via a plurality of linker molecules, a plurality of heparin chains each having a MW between 10-21 KDa and further wherein the number of said heparin chains attached to said plasma protein is selected from the group comprising 4, 5, 6, 7, 8, 9, 10, 11, 12, 13, 14, 15, and 16 for use in the manufacture of a medicament for treating Ischemia reperfusion injury or acute kidney injury or myocardial infarction or stroke or peripheral arterial occlusive disease or mesenterial ischemia.

According to a seventh aspect of the invention there is provided a method for the manufacture of an anti-thrombotic molecule having both antiplatelet and anticoagulant (APAC) activity comprising:
  i) modifying an unfractionated heparin (Hep) chain to produce a reactant product having a sulfhydryl (—SH) group;
  ii) modifying a plasma protein, such as serum albumin, to produce a reactant product having a pyridyl dithiol (-PDP) group; and
  iii) linking the reactant product of i) with the reactant product of ii) using a hetero-bi-functional cross-linker.

In a preferred method of the invention said linker is 3-(2-Pyridyldithio)propionic acid N-hydroxysuccinimide ester SPDP linker (available commercially (optionally GMP quality) for example from Sigma-Aldrich or Thermo Scientific Pierce).

According to an eighth aspect of the invention there is provided a method for the manufacture of an anti-thrombotic molecule having both antiplatelet and anticoagulant (APAC) activity comprising:
  i) modifying an unfractionated heparin (Hep) chain to produce a reactant product having a N-hydroxysuccinimide ester (—NHS) group;
  ii) linking the reactant product of i) with a plasma protein, such as serum albumin, containing primary amines using a homo-bi-functional cross-linker In a preferred method of the invention said linker is 3,3'-Dithiodipropionicacid di(N-hydroxysuccinimide ester DTSP linker (available commercially (optionally GMP quality) for example from Sigma-Aldrich or Thermo Scientific Pierce).

According to an ninth aspect of the invention there is provided a method for the treatment of a disease or condition selected from the group comprising:
thrombotic complications, such as those associated with endogenous rupture of an atheromatous plaque; thrombolytic therapy to prevent re-occlusion; platelet-driven arterial thrombosis; vascular or microvascular injuries; thrombotic thrombocytopenic purpura; ischemia reperfusion injury; acute kidney injury; myocardial infarction; stroke; peripheral arterial occlusive disease, mesenterial ischemia and Antithrombin (AT) deficiency;
wherein an effective amount of anti-thrombotic molecule having both antiplatelet and anticoagulant (APAC) activity comprising a plasma protein to which there is attached, via a plurality of linker molecules, a plurality of heparin chains each having a MW between 10-21 KDa and further wherein the number of said heparin chains attached to said plasma protein is selected from the group comprising 4, 5, 6, 7, 8, 9, 10, 11, 12, 13, 14, 15, and 16 is administered to an individual to be treated.

In a preferred embodiment of this aspect of the invention said anti-thrombotic molecule is administered after thrombolytic therapy to prevent re-occlusion.

More preferably still, said number of heparin chains is selected from the group comprising 8, 9, 10, 11 and 12.

According to a tenth aspect of the invention there is provided a method of treatment selected from the group comprising:
exogenous angioplasty; vascular or microvascular surgery; arterial intervention; angioplasty, in particular, percutaneous transluminal (coronary) angioplasty with or without stenting; (directional) arterectomy; peripheral or pulmonary thrombendarterectomy; and exogenous interventions such as insertion and maintenance of arterio-venous fistula or arterio-venous grafts; wherein an effective amount of anti-thrombotic molecule having both antiplatelet and anticoagulant (APAC) activity comprising a plasma protein to which there is attached, via a plurality of linker molecules, a plurality of heparin chains each having a MW between 10-21 KDa and further wherein the number of said heparin chains attached to said plasma protein is selected from the group comprising 4, 5, 6, 7, 8, 9, 10, 11, 12, 13, 14, 15, and 16 is administered to an individual to be treated before, during or after said treatment.

In a preferred embodiment of this aspect of the invention said anti-thrombotic molecule is administered before any one or more of the above treatments is/are performed.

More preferably still, said number of heparin chains is selected from the group comprising 8, 9, 10, 11 and 12.

More preferably still, the anti-thrombotic molecule having both antiplatelet and anticoagulant (APAC) activity was purified by chromatography such as hydrophobic interaction chromatography (HIC) using Butyl Sepharose media (GE Healthcare, USA) and/or ultra/diafiltration. However, the APAC molecules can be purified by other means, such as anion exchange chromatography, or other ways known to those skilled in the art.

In the claims which follow and in the preceding description of the invention, except where the context requires otherwise due to express language or necessary implication, the word "comprises", or variations such as "comprises" or "comprising" is used in an inclusive sense, i.e. to specify the presence of the stated features but not to preclude the presence or addition of further features in various embodiments of the invention.

All references, including any patent or patent application, cited in this specification are hereby incorporated by reference. No admission is made that any reference constitutes prior art. Further, no admission is made that any of the prior art constitutes part of the common general knowledge in the art.

Preferred features of each aspect of the invention may be as described in connection with any of the other aspects.

Other features of the present invention will become apparent from the following examples. Generally speaking, the invention extends to any novel one, or any novel combination, of the features disclosed in this specification (including the accompanying claims and drawings). Thus, features, integers, characteristics, compounds or chemical moieties described in conjunction with a particular aspect, embodiment or example of the invention are to be understood to be applicable to any other aspect, embodiment or example described herein, unless incompatible therewith.

Moreover, unless stated otherwise, any feature disclosed herein may be replaced by an alternative feature serving the same or a similar purpose.

BRIEF DESCRIPTION OF THE DRAWINGS

The present invention will now be described by way of example only with particular reference to the following figures wherein.

In comparison, with APAC treatment (open circle) the fresh injury site remained open for the duration of the entire experiment: First for 120 min at the arterial blood flow of 100 mL/min (open circle), secondly for 14 min with tightened stenosis (60%) at the arterial blood flow of 50 mL/min (black cross), and finally for 10 and 15 min sequential periods at harsh stenosis (90%) at blood flow of 30 mL/min (black stars).

Figure 16A:
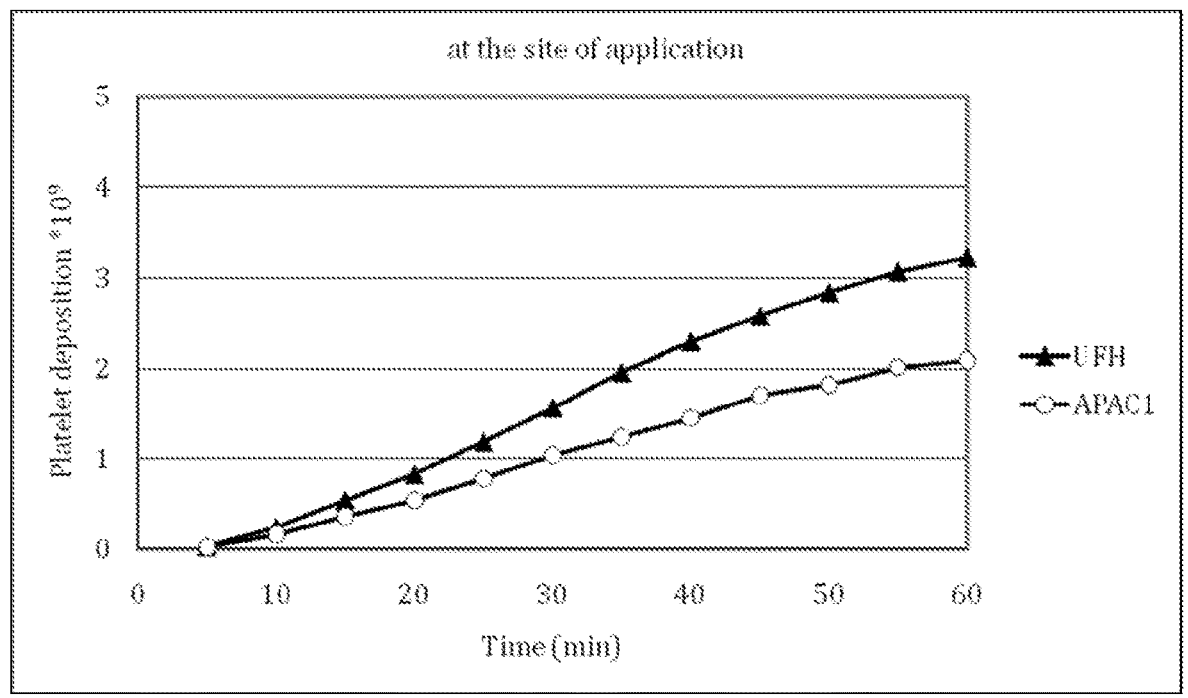

FIG. 16A. Shows a comparison of APAC1 (batch 1.1, 4 Hep chains) and UFH (both at 4 mg/mL) in collagen-induced thrombus formation in flowing blood in a baboon model (n=4). Reduced platelet deposition was observed for collagen surfaces at the site of application where the platelet deposition was reduced in the presence of APAC1 by 34±13% (mean and SD, n=4) in comparison with UFH (p=0.01). Fibrin formation was also reduced by 45%±14% (mean and SD, n=4) (p=0.01) with APAC1 in comparison with untreated control, compatible with the dual action of platelet and coagulation inhibition.

Figure 16B:
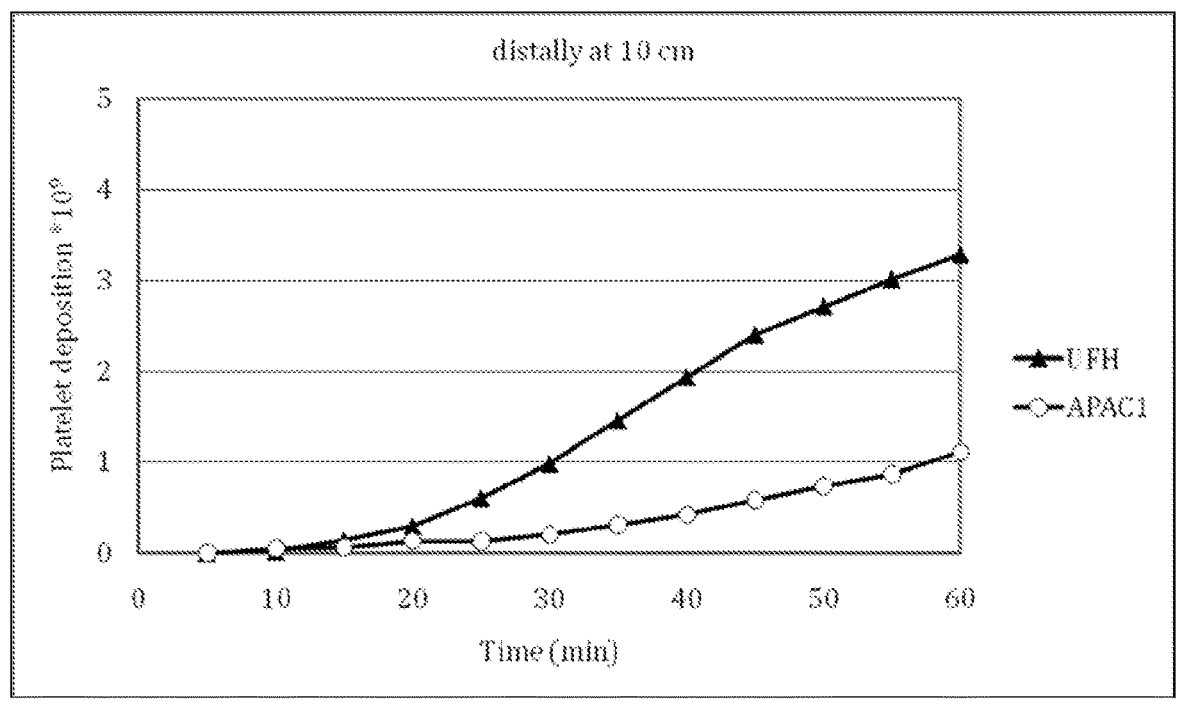

FIG. 16B. Shows a comparison of APAC1 (batch 1.1, 4 Hep chains) and UFH (both at 4 mg/mL) in collagen-induced thrombus formation in flowing blood in a baboon model (n=4). Reduced platelet deposition was observed for: thrombus that propagated 10-cm distal to the collagen segment where the platelet deposition was reduced in the presence of APAC1 by 63±11% (mean and SD, n=4) in comparison with UFH (p=0.19). Fibrin formation was also reduced by 45%±14% (mean and SD, n=4) (p=0.01) with APAC1 in comparison with untreated control, compatible with the dual action of platelet and coagulation inhibition.

Figure 17:
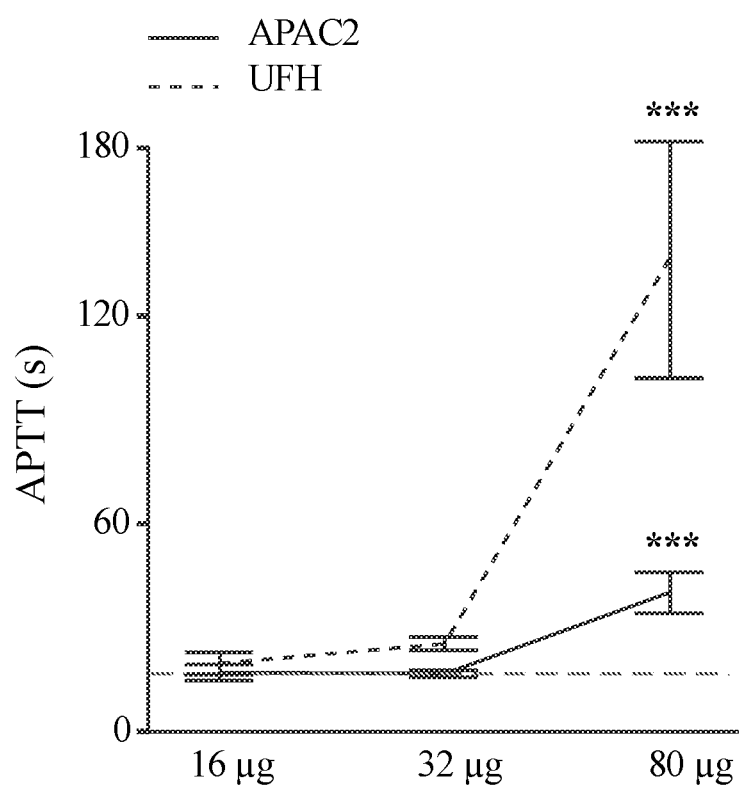

FIG. 17. Shows the immediate anticoagulant action of APAC and UFH in rat plasma. The APAC2 (batch 2.1, 11 Hep chains), used at 16, 32 or 80 µg to investigate ischemia reperfusion injury or acute kidney injury were effective anti-coagulants when measured using a APTT assay. As a comparator, unfractionated heparin (UFH, dotted black line) was used at the same concentration range 16, 32 or 80 µg. It can be seen that the two therapeutics performed comparatively equally at 16 µg but at 32 µg UFH prolonged the APTT marginally more than APAC2, whereas at 80 µg UFH prolonged the APTT significantly more than APAC2 (solid black line).

APTT as mean±SD 10 min after i.v. administration of APAC2 or UFH at the dose of 16 µg (0.06 mg/kg), 32 µg (0.13 mg/kg) and 80 µg (0.32 mg/kg). n=5-8/group. ***$P<0.001$. At the dose of 16 µg, APTT was 18.0±6.6 (n=7) with APAC and 27±6.2 (n=4), with UFH. At the dose of 32 µg, APTT was 17.4±4.0 (n=10) with APAC and 25.2±2.0 (n=5), with UFH. At the dose of 80 µg, APTT was 42.2±18 (n=8), with APAC and 72-180> (n=5), with UFH. The dotted red line is the baseline reference for APTT. Heparin doses were determined using UFH as the standard in Blyscan Sulfated Glycosaminoglycan assay.

Figure 18A:
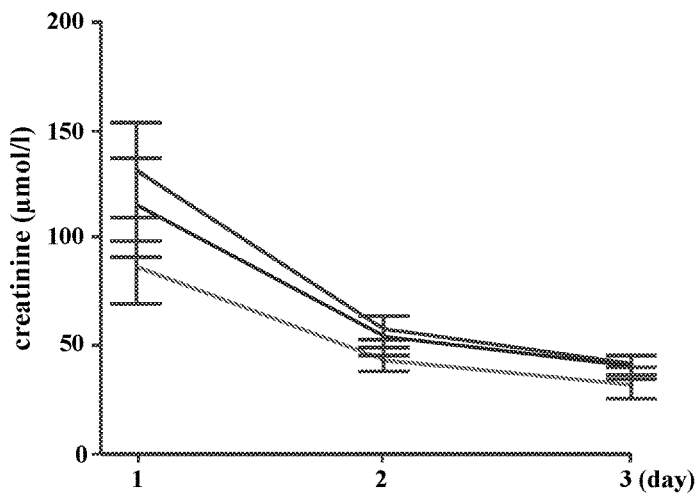

FIG. 18A. Shows kidney function and tubulointerstitial injury after 30-min bilateral kidney ischemia-reperfusion-injury. The effect of 16 or 32 µg of APAC2 (batch 2.1, 11 Hep chains) on kidney function, when assayed using established markers, compared to a control of saline vehicle (i.v.) only. The kidney function markers creatinine, urea and neutrophil gelatinase-associated lipocalin (NGAL) were assayed over a three day period following reversible ischemia reperfusion injury of 30 min and the concentration of APAC2 of 32 µg significantly reduced the levels of each marker at every time interval; implying a protective role for the APAC2 at 32 µg.

To analyze the kidney function and tubulointerstitial injury after the renal ischemia, rat serum was collected daily for 3 days after reperfusion. Serum levels of creatinine were measured in APAC 16 µg (0.06 mg/kg) and 32 µg (0.13 mg/kg) i.v. pretreated rats. Control rats received saline vehicle i.v. n=8/group. **$P<0.01$. Heparin doses were determined using UFH as the standard in Blyscan Sulfated Glycosaminoglycan assay.

Figure 18B:
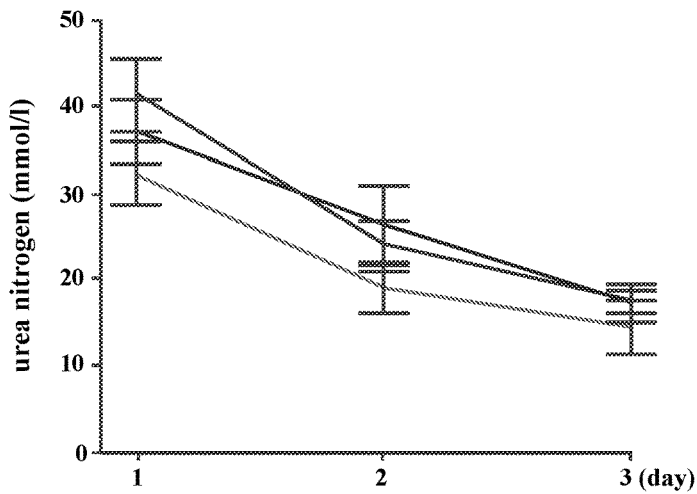

FIG. 18B. Shows kidney function and tubulointerstitial injury after 30-min bilateral kidney ischemia-reperfusion-injury. The effect of 16 or 32 µg of APAC2 (batch 2.1, 11 Hep chains) on kidney function, when assayed using established markers, compared to a control of saline vehicle (i.v.) only. The kidney function markers creatinine, urea and neutrophil gelatinase-associated lipocalin (NGAL) were assayed over a three day period following reversible ischemia reperfusion injury of 30 min and the concentration of APAC2 of 32 µg significantly reduced the levels of each marker at every time interval; implying a protective role for the APAC2 at 32 µg.

To analyze the kidney function and tubulointerstitial injury after the renal ischemia, rat serum was collected daily for 3 days after reperfusion. Serum levels of urea nitrogen were measure in APAC 16 µg (0.06 mg/kg) and 32 µg (0.13 mg/kg) i.v. pretreated rats. Control rats received saline vehicle i.v. n=8/group. **$P<0.01$. Heparin doses were determined using UFH as the standard in Blyscan Sulfated Glycosaminoglycan assay.

Figure 18C:
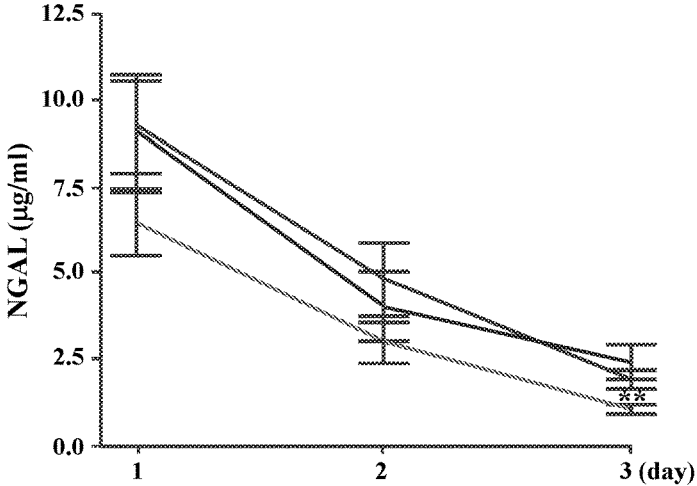

FIG. 18C. Shows kidney function and tubulointerstitial injury after 30-min bilateral kidney ischemia-reperfusion-injury. The effect of 16 or 32 µg of APAC2 (batch 2.1, 11 Hep chains) on kidney function, when assayed using established markers, compared to a control of saline vehicle (i.v.) only. The kidney function markers creatinine, urea and neutrophil gelatinase-associated lipocalin (NGAL) were assayed over a three day period following reversible ischemia reperfusion injury of 30 min and the concentration of APAC2 of 32 µg significantly reduced the levels of each marker at every time interval; implying a protective role for the APAC2 at 32 µg.

To analyze the kidney function and tubulointerstitial injury after the renal ischemia, rat serum was collected daily for 3 days after reperfusion. Serum levels of NGAL, a biomarker of tubulointerstitial injury, were measured in APAC 16 µg (0.06 mg/kg) and 32 µg (0.13 mg/kg) i.v. pretreated rats. Control rats received saline vehicle i.v. n=8/group. **P<0.01. Heparin doses were determined using UFH as the standard in Blyscan Sulfated Glycosaminoglycan assay.

Figure 19A:
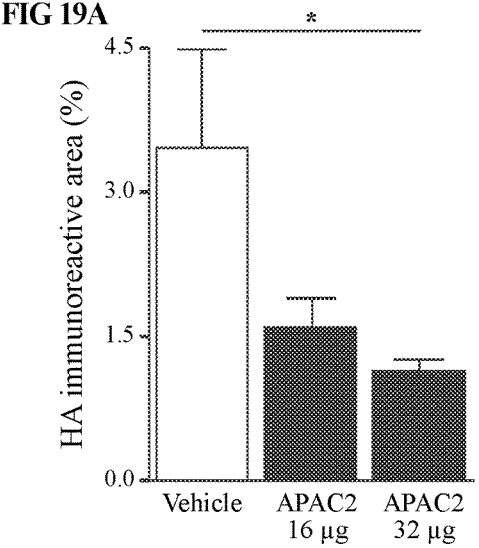

FIG. 19A. Shows innate immune activation measured as innate immunity ligand hyaluronin (HA) immunoreactive area (%) after 30-min bilateral kidney ischemia-reperfusion injury. The visible effects of ischemia reperfusion injury after 30 min reversible injury were ameliorated by the use of APAC2 (batch 2.1, 11 Hep chains) at either 16 or 32 µg compared to saline vehicle (i.v.) control. Control rats received saline vehicle i.v. IgG controls in the insets. n=8/group. *P<0.05. Heparin doses were determined using UFH as the standard in Blyscan Sulfated Glycosaminoglycan assay.

Figure 19B:
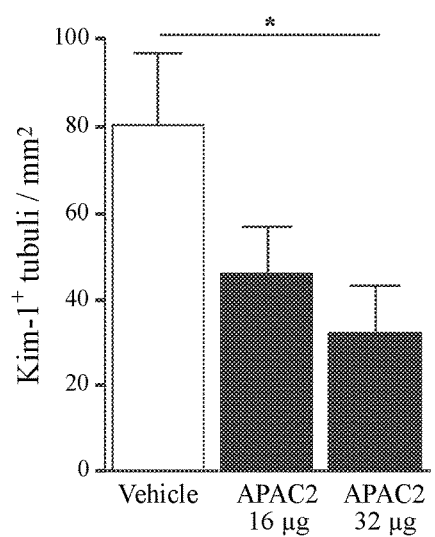

FIG. 19B. Shows innate immune activation determined as tubular damage measured by tubulointerstitial injury marker Kim-1 (Kim-1$^+$ tubuli/mm$^2$) after 30-min bilateral kidney ischemia-reperfusion injury. The visible effects of ischemia reperfusion injury after 30 min reversible injury were ameliorated by the use of APAC2 (batch 2.1, 11 Hep chains) at either 16 or 32 µg compared to saline vehicle (i.v.) control. Control rats received saline vehicle i.v. IgG controls in the insets. n=8/group. *P<0.05. Heparin doses were determined using UFH as the standard in Blyscan Sulfated Glycosaminoglycan assay.

Figure 19C:
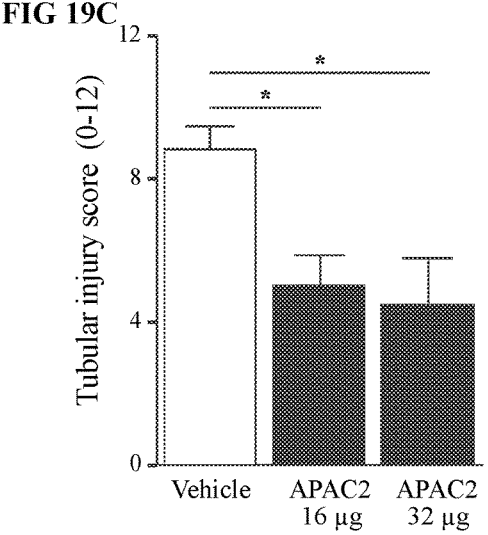

FIG. 19C. Shows innate immune activation measured as tubular injury score (0-12) determined by hematoxylin and eosin (H&E) staining after 30-min bilateral kidney ischemia-reperfusion-injury. The visible effects of ischemia reperfusion injury after 30 min reversible injury were ameliorated by the use of APAC2 (batch 2.1, 11 Hep chains) at either 16 or 32 µg compared to saline vehicle (i.v.) control. Control rats received saline vehicle i.v. IgG controls in the insets. n=8/group. *P<0.05. Heparin doses were determined using UFH as the standard in Blyscan Sulfated Glycosaminoglycan assay.

Figure 19D:
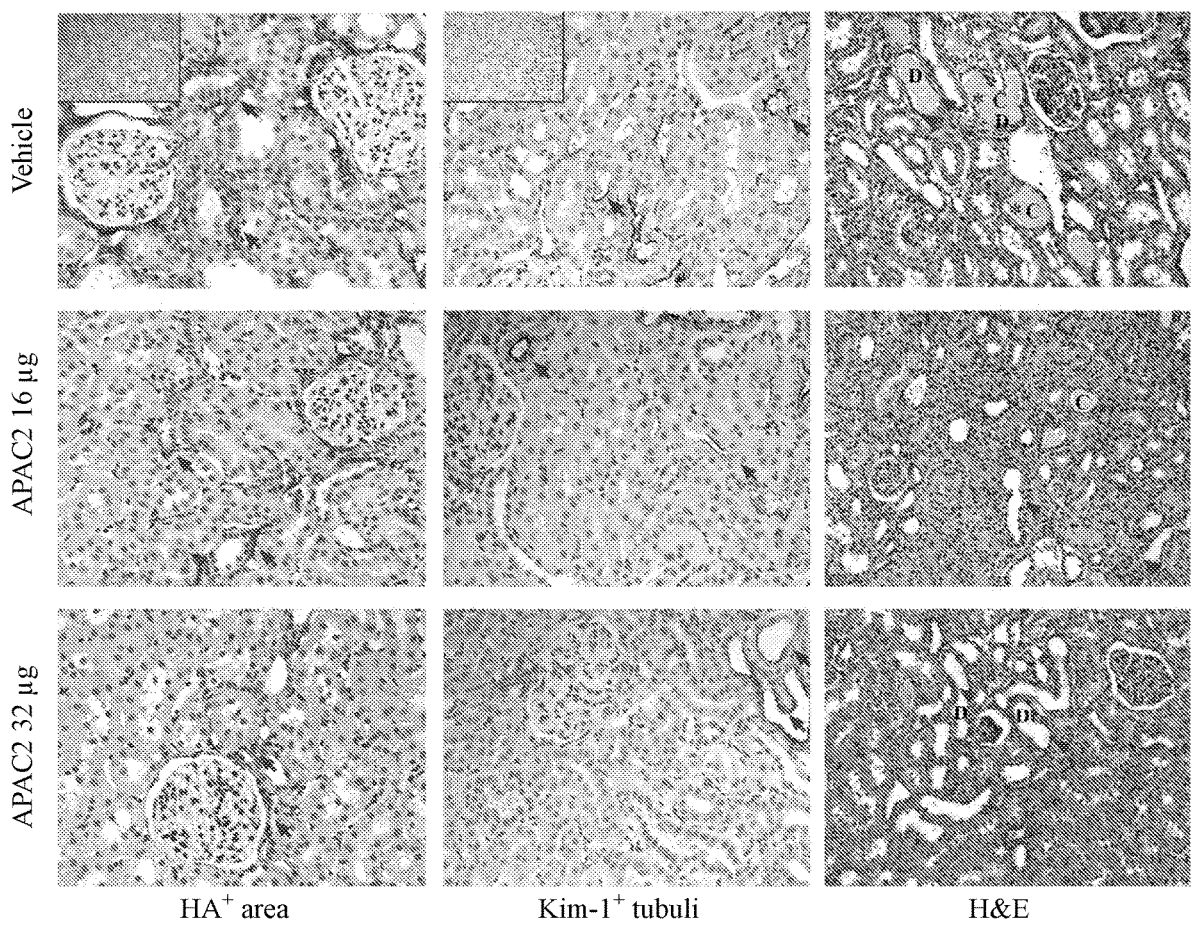

FIG. 19D. Shows histopathology by staining for HA (first column), for Kim-1 (second column), and for H&E (third column) after 30-min bilateral kidney ischemia-reperfusion-injury. The visible effects of ischemia reperfusion injury after 30 min reversible injury were ameliorated by the use of APAC2 (batch 2.1, 11 Hep chains) at either 16 or 32 µg compared to saline vehicle (i.v.) control. For assessment of the innate immune activation and renal injury at 3 days after reperfusion, kidney paraffin-embedded cross-sections were stained for innate immunity ligand hyaluronan, tubulointerstitial injury marker Kim-1, and H&E for histopathology in APAC 16 µg (0.06 mg/kg) and 32 µg (0.13 mg/kg) i.v. pretreated rats. The area positive for hyaluronan was measured with computer assisted imaging. For the H&E-stained cross-sections, C=epithelial casts; D=tubular dilatation; arrowhead=epithelial flattening; arrow=epithelial necrosis. Control rats received saline vehicle i.v. IgG controls in the insets. n=8/group. *P<0.05. Heparin doses were determined using UFH as the standard in Blyscan Sulfated Glycosaminoglycan assay.

Figure 20A:
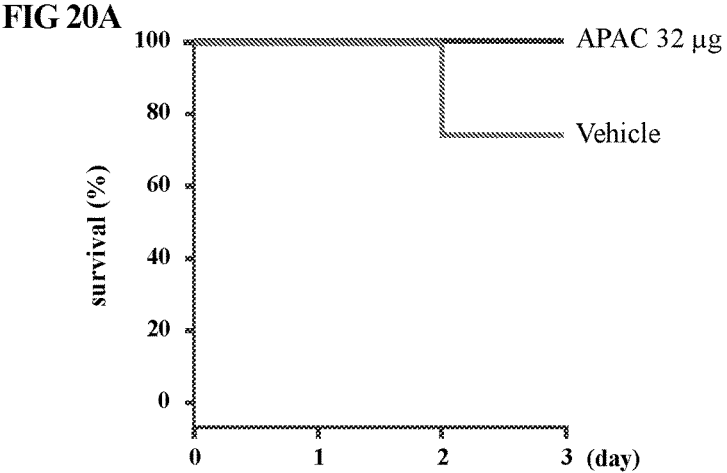

FIG. 20A. Shows % rat survival over a three day surveillance period after kidney injury and treatment with APAC (batch 2.1, 11 heparin chains, 32 µg), illustrating positive effects of APAC on kidney function and overall survival after severe one-hour bilateral kidney ischemia-reperfusion-injury. Kidneys were subjected to severe IRI in clamping both renal arteries for one hour. To analyze the post-ischemic kidney survival and function, rat serum was collected daily for 3 days after reperfusion. Control rats received saline vehicle i.v. n=8/group. *P<0.05, P<0.01, *P<0.001. Heparin doses were determined using UFH as the standard in GAG assay.

Figure 20B:
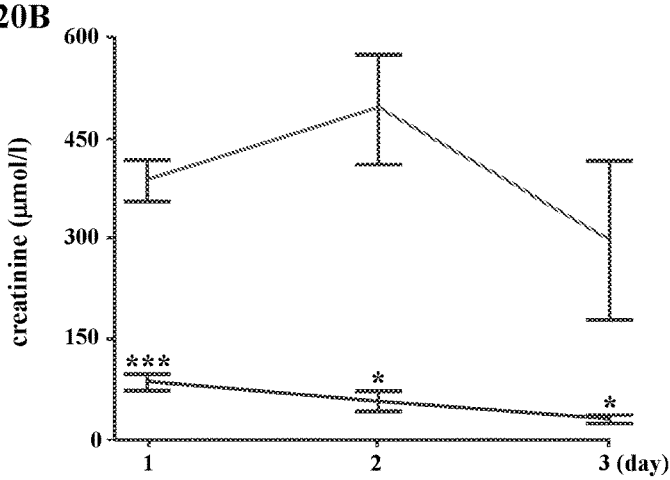

FIG. 20B. Shows serum levels of creatinine in APAC 32 µg (0.13 mg/kg) i.v. pretreated rats after kidney injury, illustrating positive effects of APAC on kidney function and overall survival after severe one-hour bilateral kidney ischemia-reperfusion-injury. Kidneys were subjected to severe IRI in clamping both renal arteries for one hour. To analyze the post-ischemic kidney survival and function, rat serum was collected daily for 3 days after reperfusion. Rat serum creatinine was reduced suggesting the retention of kidney function. Control rats received saline vehicle i.v. n=8/group. *P<0.05, P<0.01, *P<0.001. Heparin doses were determined using UFH as the standard in GAG assay.

Figure 20C:
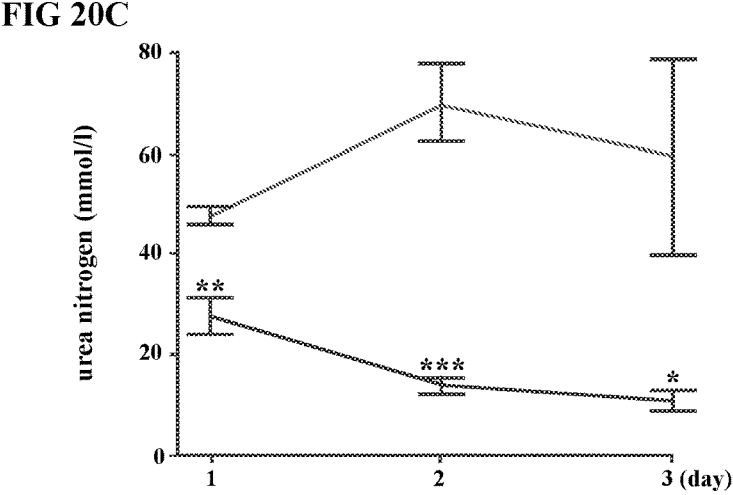

FIG. 20C. Shows serum levels of urea nitrogen in APAC 32 µg (0.13 mg/kg) i.v. pretreated rats after kidney injury, illustrating positive effects of APAC on kidney function and overall survival after severe one-hour bilateral kidney ischemia-reperfusion-injury. Kidneys were subjected to severe IRI in clamping both renal arteries for one hour. To analyze the post-ischemic kidney survival and function, rat serum was collected daily for 3 days after reperfusion. Rat serum urea was reduced suggesting the retention of kidney function. Control rats received saline vehicle i.v. n=8/group. *P<0.05, P<0.01, *P<0.001. Heparin doses were determined using UFH as the standard in GAG assay.

Figure 21:
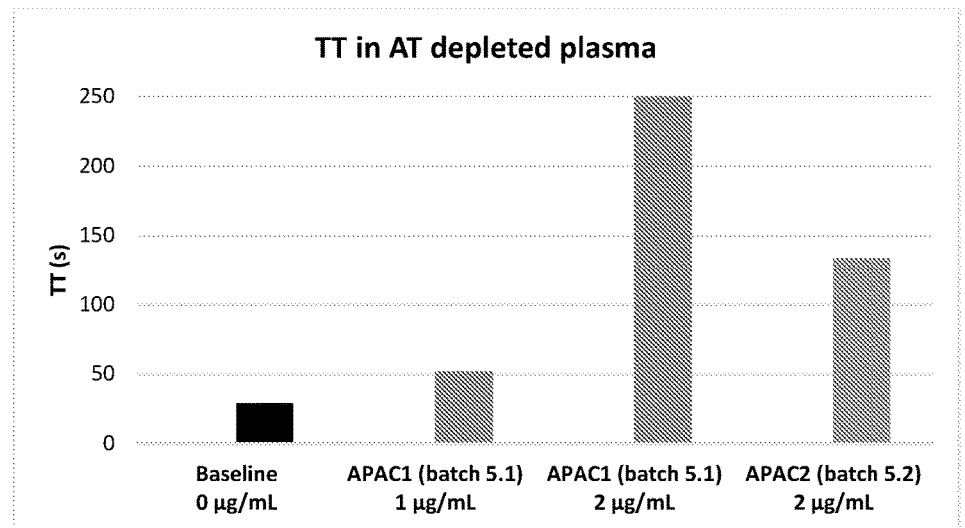

FIG. 21. Shows thrombin time (TT) in the presence of the fifth generation APAC1 (batch 5.1, 4 Hep chains) at Hep [C] of 1.0 and 2 µg/mL and APAC2 (batch 5.2, 8 Hep chains) at Hep [C] of 2 µg/mL in antithrombin-depleted plasma. Heparin doses were determined using UFH as the standard in GAG assay.

Figure 22:
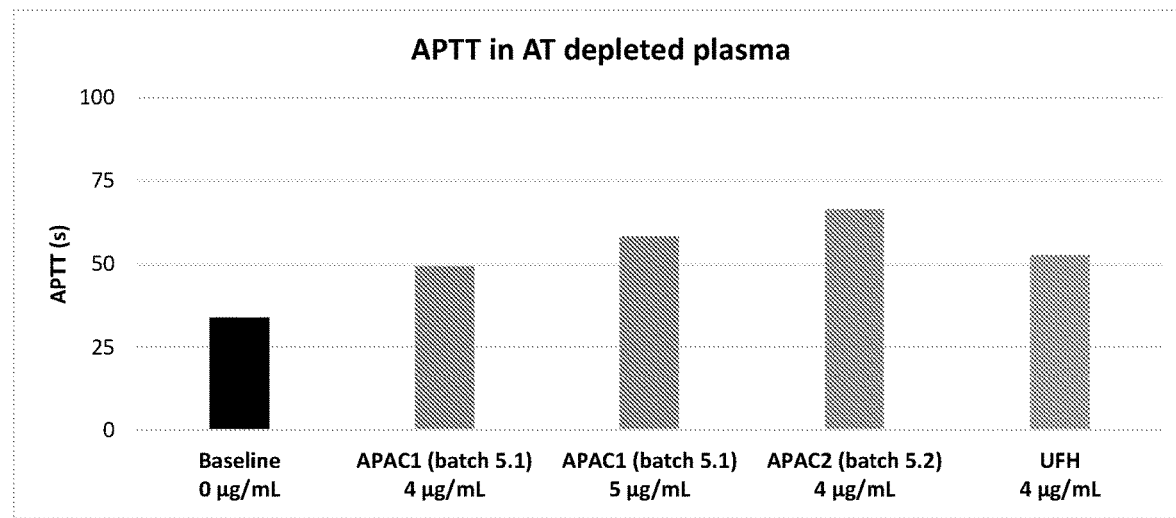

FIG. 22. Shows activated partial thromboplastin time (APTT) in the presence of the fifth generation APAC1 (batch 5.1, 4 Hep chains) at Hep [C] 4 and 5 µg/mL, and APAC2 (batch 5.2, 8 Hep chains) and UFH at Hep [C] 4 µg/mL in antithrombin depleted plasma. Heparin doses were determined using UFH as the standard in GAG assay.

DETAILED DESCRIPTION

Methods
Conjugation

Unfractionated heparin (Hep) chains were conjugated to Human Serum Albumin (HSA) through disulfide bridges created by two alternative cross-linkers and reactions routes using:
i) hetero-bi-functional cross-linker 3-(2-Pyridyldithio) propionic acid N-hydroxysuccinimide ester (SPDP). For the conjugation free amines on Ser at the Hep linker region and Lys on HSA were utilized. Hep and HSA were modified in separate reactions into sulfhydryl (—SH)- and pyridyl dithiol (-PDP)-derivatives, respectively. In the final conjugation reaction the pyridyldithiol-group of HSA reacted with sulfhydryl group of Hep resulting in the formation of a disulphide bonded complex and the release of pyridine 2-thione.

ii) homo-bi-functional cross-linker 3,3'-Dithiodipropionicacid di(N-hydroxysuccinimide (NHS)-ester) (DTSP). For the conjugation, free amines on Ser at the Hep linker region and Lys on HSA were utilized. Hep was first modified into N-hydroxysuccinimide (NHS)-ester-derivative with the release of the first NHS-group. In the final conjugation reaction the Lys of HSA reacted with the N-hydroxysuccinimide (NHS)-ester group of the derivatized Hep, resulting in the formation of a complex with a cleavable disulfide bond in the linker region and the release of the second N-hydroxy-succinimide group.

Hep-HSA complexes were purified by hydrophobic interaction chromatography (HIC) using Butyl Sepharose media (GE Healthcare, USA) or ultra/dialfiltration. At the end Hep-HSA complexes were eluted into phosphate buffered saline (PBS) with pH 7.4. Complexes were named as APAC- with a suffix extension designating the conjugation level of Hep chains to HSA.

The general formula for APAC complexes that exemplify the invention is

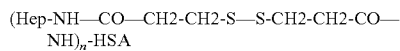

where the average number of unfractionated heparin chains coupled to HSA is defined as n.

The mean conjugation level (CL) of Hep to HSA was determined using the concentration of Hep and HSA and their average molecular weights with the following equations:

mol of Hep=Hep [C]/mean Hep MW
mol of HSA=HSA [C]/HSA MW
CL=mol of Hep/mol of HSA
Hep MW=15800
HSA MW=66472

The mean MW for the Hep polymer is based on the information obtained from the heparin manufacturer. HSA MW is based on ALBU_HUMAN, P02768 from UniProtKB/Swiss-Prot, isoform 1 without signal- and propeptide. APAC complexes. See Table I.

APAC1 has a mean CL of 4-6 mol Hep per 1 mol HSA.
APAC2 has a mean CL of 8-16 mol Hep per 1 mol HSA.

In 2010, a first generation of APACs, i.e. APAC1 was manufactured on a relatively large (Ig) scale having a mean CL of 6 mol Hep per 1 mol HSA (CL 6:1; batch 1.1). APAC1 showed both anticoagulant and antiplatelet efficacies in vitro. In two different baboon models of acute thrombosis, it maintained the vessel patency and reduced both thrombosis and fibrin accumulation relative to a control that was unfractionated heparin (UFH), i.e. heparin that was not coupled to HSA. Also, radioactively (Cu-64) labelled APAC1 had prolonged localization at the site of topical administration on a fresh rat anastomosis compared to the control i.e. UFH (study at IPS Therapeutics, Canada).

In 2011, a second generation of APACs named as APAC2 (batch 2.1), was manufactured having almost double the mean CL (11:1) of Hep to HSA when compared to APAC1. When compared to APAC1, APAC2 was more efficient in inhibiting collagen-induced platelet aggregation in platelet-rich plasma (PRP) at the same heparin concentration. In a rat anastomosis model, Cu-64 labelled APAC2 was administered inside the vessel and was detectable for twice the time of UFH control (IPST, Canada).

In 2012, a third generation APACs (this time in multiple batches 3.1 to 3.6) was manufactured. Six different APAC complexes (with CL 6:1 to 16:1), were manufactured in a small scale (batch sizes of ~50 mg) in order to study the reproducibility of the conjugation reaction (CR) itself. These APAC complexes were named (CR1 to 6) according to the manufacturing order and so these names therefore do not reflect the specific CL of the products. As manufacturing protocol was adjusted for the small scale, accordant changes may have slightly modified the final characteristics of the products. Interestingly and uniformly, the compounds with higher CL were more efficacious than lower CL in inhibiting collagen-induced platelet aggregation in PRP. On the other hand, the anticoagulant efficacy seemed more pronounced with lower CL.

In 2013, a fourth generation of APACs, both APAC1 (CL 4:1; batch 4.1) and APAC2 (CL 8:1; batch 4.2), were manufactured.

In 2014, a fifth generation of APACs, was made APAC1 (CL 4:1; batch 5.1) and APAC2 (CL 8:1; batch 5.2). Analysis of the 2014 batches is ongoing.

Quantification

Determining the CL of the APAC products has been demanding because of the nature of the conjugated molecules, i.e. having both HSA protein and highly sulphated heparin moieties. HSA concentration was determined with bicinchonic acid (BCA) protein assay according to manufacturer's instructions (Pierce Biotechnology, USA). In 2013, direct UV-measurement at 280 nm was also undertaken to validate the BCA assay because the BCA assay seemed to overestimate the protein. Hep (Heparin Leo, Leo Pharma, Denmark) was determined with Blyscan Sulfated Glycosaminoglycan assay according to manufacturer's instructions (Biocolor Ltd., UK), Blyscan assay.

In 2010 and 2012, Hep was assayed against glycosaminoglycan (GAG) standard (bovine tracheal chondroitin 4-sulphate). With this GAG standard the Hep concentration was typically overestimated. Therefore, in 2013 heparin starting material was included as a new standard for the Blyscan assay. For thoroughness and comparative reasons both GAG and heparin were used for the subsequent analysis. Determination of the CL was influenced by the specific standard used in the heparin assay (Table I) and also by the analysis of HSA. Nevertheless, in all studies where different APACs and control UFH have been compared, Hep concentrations were determined with the same assay, whether GAG or more recently Hep standard (Sulphated glycosaminoglycan assay, Blyscan Assay Kit, Biocolor Ltd., UK).

Briefly, test samples to be quantified were added to micro-centrifuge tubes and volume adjusted to 100 μl using water. With each assay, Blyscan Assay Kit sulfated GAG standard or a known heparin standard was also run at the specified concentration range in addition to a reagent blank (0 μg; water or PBS). To begin the assay, 1.0 ml of Blyscan Dye reagent was added (1,9-dimethyl-methylene blue in inorganic buffer) and mixed for at least 30 min. Tubes containing sulphated heparin turned purple/pink. The resulting GAG-dye complex was separated from unbound dye by centrifugation (>10,000×g for 10 minutes). Supernatants were discarded and 1.0 ml Blyscan Dissociation Reagent was added and vortexed. The resulting solution was then assayed by spectrophotometric readings at 656 nm. The standards, along with the reagent blank, were used to produce a calibration curve, which was utilized to determine heparin concentration. Absorbance values were between 0.05 and 1.5 units, otherwise samples were reconstituted or diluted, respectively.

Molecular Weights

Molecular weights (MW) for the APACs have not been finalised yet, and the molarity of the solutions can only be approximated. Studies with regular size exclusion chromatography (SEC) and with the combined high pressure SEC and triple detector array (TDA; with refractometer, viscometer and left and right angle light scattering detectors) technique indicate, roughly, a doubling increase in the MW between APAC1 (batch 1.1) and APAC2 (batch 2.1).

Assessment of APAC Function In Vitro

Materials and Methods

Blood Collection

Blood from healthy donors who had not taken any medications for at least 6-7 days preceding sample collection was used. Samples were collected after an overnight fast via a venipuncture, from the antecubital vein into standard vacuum blood-collection tubes (0.109 M sodium citrate Vacuette 455322, Greiner Bio-one). The sample was considered valid for 4 hours after blood collection.

Platelet-Rich Plasma and Platelet-Poor Plasma

Blood was centrifuged at 180×g for 12 min at 22 degree Celsius to separate platelet-rich plasma (PRP). For platelet-poor plasma (PPP) collection, the remnant blood was centrifuged again at 1500×g for 10 min at 22 degree Celsius. Platelet (PLT) number in PRP was measured with cell counter Sysmex KX-21 (Sysmex Corporation, Japan) and adjusted with PPP to $150*10^6$ 10% PLT/mL for Calibrated Automated Thrombogram (CAT) analysis and to $300*10^6 \pm 10\%$ PLT/mL for agonist-induced PRP aggregation. For the in house plasma pool, blood from 11 donors was collected and centrifuged at 2000×g for 10 min. The PPP was re-centrifuged at 10.000×g for 10 min to remove any remaining platelets. Plasmas were combined, and stored in aliquots and frozen until use. For CAT plasma was centrifuged twice.

Plasmas

The anticoagulant efficacy of APAC complexes and UFH control was tested at equal heparin concentrations (Blyscan GAG st.). Three different plasmas were used: laboratory control plasma, i.e. standard human plasma (SHP, Siemens, Germany), solvent/detergent (S/D)-treated plasma (Octaplas, Octapharma, Switzerland), and in house pooled plasma (PP, 11 healthy donors). In this summary, results in the in house pooled plasma are shown as examples.

Antithrombin (AT)-depleted plasma (American Diagnostica, USA) was used to study the AT-independent anticoagulant efficacy of APACs and, in an APTT assay, UFH.

Coagulation

Heparin binds the complex of antithrombin and thrombin (IIa) and potentiates the ability of antithrombin to inactive thrombin and coagulation factor Xa and several other coagulation factors upstream of the intrinsic and extrinsic pathways of coagulation. In contrast, low molecular weight heparins (LMWH) bind only to antithrombin to inhibit nearly exclusively factor Xa. The thrombin targeting demands longer chain lengths; needing at least 18 unit sequences of pentasaccharide in the heparin. The anticoagulant efficacy of heparin-containing plasma samples is tested routinely by the time of fibrin clot formation in PPP, devoid of platelets and other blood cells. Heparin is highly sulphated and possesses a strong negative charge. Thus, non-specific binding to circulating plasma proteins or vessel endothelium may induce other interactions not explored here.

Thrombin Time

In thrombin time (TT) (Thrombin BC reagent, Siemens, Germany) assay diluted (40 μL plasma and 100 μL of Thrombin BC) citrated plasma is supplemented with standardised high dose of thrombin (0.8 IU/ml), and the time for the conversion of fibrinogen to fibrin clot is measured in a coagulometer (KC-4, Sigma-Amelung, USA).

Activated Partial Thromboplastin Time

In activated partial thromboplastin time (APTT, reagent Dade Actin FSL, Siemens, USA) assay, clot formation is induced by the coagulation factors of the intrinsic pathway (I, II, V, VIII, IX, X, XI, XII), representing contact activation and by re-calcification of the plasma. In the experiment, 50 μL of plasma is diluted with 50 μL of Actin FSL (soy and rabbit brain phospholipids in 100 μM ellagic acid) and re-calcified with 50 μL of 25 mM $CaCl_2$). In the presence of sufficient amount of heparin, TT and APTT start to dose-dependently prolong. Clinically the extent of intravenously administered heparin anticoagulation is monitored mainly with APTT. In order to reach the therapeutic level of anticoagulation, 1.5- to 3-fold prolongation over the control sample is targeted. APTT assay is dependent on the reagent and the coagulometer used, but the baseline range is typically 20-40 s.

Calibrated Automated Thrombogram

Thrombin generation is experimentally used to estimate conditions associated with the risk of bleeding or thrombosis (Hemker et al. Pathophysiol Haemost Thromb 2002; 32:249-53). Although thrombin is formed during the entire coagulation process, only 2 to 5% of the total thrombin is needed for fibrin to clot in vitro. Therefore, the traditional coagulation times (i.e. TT and APTT) overlook the majority of thrombin activity during coagulation, which can be captured by Hemker's method Calibrated Automated Thrombogram (CAT). CAT assesses tissue factor-triggered thrombin generation, which is monitored by detecting the splitting of a fluorogenic thrombin substrate and parallel comparison of the sample with a control having known thrombin activity. In the course of thrombin generation, both the anti- and pro-coagulant factors influence the measurable characteristics of the Thrombogram. The lag time reflects the time of the fibrin clot formation reflecting PT (is triggered with tissue factor (TF)/APTT (is triggered with ellagic acid). The peak of the curve shows the maximal rate of net thrombin generation and the time to reach it (ttpeak). The area under the curve, i.e. the endogenous thrombin potential (ETP), measures the total thrombin formed. In CAT, thrombin generation can be assessed either in citrated PPP or PRP. Thrombin is activated in re-calcified plasma by triggering and supplementing samples with TF (5 pM) and phospholipids (PPL) (4 μM) (PPP reagent, Stago, France) or with TF (1 pM, PRP reagent, Stago, France) for PPP and PRP, respectively. CAT is able to detect the deficiencies or hyper-activity of clotting factors, and the use of anti-coagulants (like heparins or direct thrombin inhibitors), or replacement therapies in case of bleeding disorders.

Platelet Aggregation in PRP

Platelet aggregation was studied with turbidometric method of Born (J Physiol 1962; 162:67-68) using Aggram aggregometer (Helena Laboratories Inc., USA) at 37° C. with the stir bar speed of 1000 r.p.m. Collagen (type I fibrils, Kollagenreagens-Horm, Nycomed Pharma, Austria or Chronolog collagen, Chronolog Ltd., USA) was used as the main agonist at the final concentration of 0.5 μg/mL. Prior to inducing platelet aggregation the test substances were incubated for 2 min with PRP at 22° Celsius and for 1 min at 37° Celsius. Maximal aggregation at 5 min (% change of light transmission), slope and area under the curve were measured when applicable.

In all assays, the baseline was measured with the vehicle (PBS, pH7.4) at the equivalent volume to the test substances. We have also studied other agonists; adenosine di-phosphate (ADP), ristocetin and collagen-related peptide (CRP). APACs do not inhibit ADP-induced platelet aggregation, while at high concentrations ristocetin-induced aggregation is inhibited (data not shown). The antiplatelet activity of APACs against collagen is the most outstanding feature in platelet aggregation tests.

Models of Acute Thrombosis in Baboons

The antithrombotic efficacy of APAC1 (batch 1.1) and UFH in comparison with vehicle was studied in two well established models of acute thrombosis in anesthetized baboons. In a modified Folts' model an extracorporeal AV-shunt was created between femoral artery and vein. The blood flow was controlled by an external constrictor placed on the artery and flow was monitored with a probe. The artery was injured from outside by cross-clamping twice for 10 s with a Martin needle holder (Hegar-Baumgartner TC Gold 14 cm). All side branches in the proximity of the injury were ligated. The shunt was punctured with a needle (26 G) 1 cm proximal to the vascular access for injecting a bolus (4 mg/mL) of either APAC1 or UFH or phosphate buffered saline (PBS). The injury was treated for 3 min with the study substance prior to expose to blood flow. Immediately after recovering the baseline blood flow an external constrictor was placed on the injury and flow was reduced to 30-100 mL/min (a stenosis of 90 to 30%). The accumulation of platelets on the stenosed artery was detected by the reduced blood flow and recorded as cyclic flow reductions (CFR). At 5 mL/min the artery was considered occluded, and the thrombus was dislodged by releasing the constrictor and flushing with phosphate buffered saline (PBS). After baseline blood flow was recovered stenosis was reapplied and experiment repeated.

In the second baboon model, thrombosis was induced by placing collagen-coated PTFE grafts (2 cm, 4 mm lumen) into an externalized arterio-venous shunt. The thrombogenic collagen surface was treated for 10 min with APAC or UFH (both at 4 mg/mL). Blood flow was initiated (100 mL/min; 265-1) and the deposition of 111-Indium-labelled platelets and fibrin (accumulation of 125-Iodine-fibrinogen) was quantified for 60 min.

Retention on the Injury Site

Efficacy, distribution, and retention on-site of locally administered 64-Cu-labeled APAC or UFH (3 mg/Kg) were assessed by PET imaging for 50 h of partially ligated (2 loose sutures 1 cm apart) femoral artery anastomoses in rats.

Ischemia Reperfusion Injury and Acute Kidney Injury Model.

Animals. Specific, pathogen-free, outbred male Sprague Dawley (SD) rats (Harlan Laborato-ries; Horst, Nederland) weighing 235-250 g were used. The rats received regular rat food and tap water ad libidum, and were maintained on a 12-h light/dark cycle. The animals received human care in compliance with the Guide for the Care and Use of Laboratory Animal Re-sources published by the National Institutes of Health and Office of Animal Care and Use (National Research Council, Washington DC, National Academy Press, 1996).

Blood cell counts and coagulation profile. The SD rats were administered (n=8/group) i.v. APAC2 (batch 2.1; 16 μg, 32 μg or 80 μg or UFH 32 μg (infusion solution 5000 IU/mL; 200 IU/mg; Leo Pharma, Denmark) diluted to appropriate concentration with PBS (10 mM sodium phosphate, 137 mM sodium chloride, 2.7 mM potassium chloride at pH 7.4). Control rats received i.v. saline vehicle. At 10 minutes, rats were sacrificed for blood cell counts and coagulation profile analysis. First blood sample was drawn in a 2 mL syringe pre-filled with 3.8% sodium citrate anticoagulant and placed in 3 mL polypropylene sample tubes. Second sample was drawn immediately after to another 2 mL empty syringe for collection of rat serum. Samples were processed separately for blood cell count, PPP and plasma as well as serum. Blood cell counts were determined in the citrated blood samples with the cell counter Sysmex KX-21. For PPP blood was centrifuged at 1200×g for 15 min (22° C.) to separate leukocytes and red blood cells. Care was taken not to disturb the buffy coat while pipetting the PPP to a new tube. PPP was centrifuged a second time at 16100×g for 5 min, after which PPP was collected to a new tube. PPP was stored at −40° C. if not used immediately.

Renal artery clamping model. The SD rats received 10 min before or after the onset of warm ischemia depending on the study model, either (n=8/group) i.v. APAC2 (batch 2.1) 16 μg, 32 μg or 80 μg or UFH 32 μg (infusion solution 5000 IU/mL, 200 mg/IU) diluted to appropriate concentration with PBS. Control rats received i.v. saline vehicle. The rats were anesthetized with inhalational isoflurane and a midline abdominal incision was performed. Both renal arteries were clamped for 30 or 60 min depending on the study model. After clamp removal, the kidneys were inspected for recovering of blood flow, and the abdomen was closed. The rats were administered 1 mL of PBS and 0.1 mL of buprenorphinum (Temgesic 0.3 mg/ml, Schering-Plough, Kenilworth, NJ) for post-operative maintenance of fluid balance and pain relief, respectively.

Assessment of renal function and acute kidney injury. For the assessment of renal function and kidney injury rat tail vein blood samples were collected under anesthesia on day 1, 2, and 3 after kidney injury. Serum was frozen at −20° C. until further analysis of creatinine and urea nitrogen activities under HUSLAB clinical chemistry division, Helsinki University Hospital, Helsinki, Finland. As a biomarker for acute kidney injury, we used rat neutrophil gelatinase-associated lipocalin (NGAL). NGAL serum levels were estimated by ELISA using mouse monoclonal anti-NGAL (ABS 039-08 from BioPorto Diagnostics A/S, Gentofte, Denmark) 3 days after bilateral renal artery clamping.

Immunohistochemistry. For immunohistochemistry, 4 mm thick paraffin-embedded or cryostat cross sections were cut in series on glass slides and stained using the peroxidase ABC method (Vectastain Elite ABC Kit, Vector Laboratories). The reaction was revealed by 3-amino-9-ethylcarbazole (AEC, Vector Laboratories). For immune-staining, the specimens were blocked with a 20 min incubation with 1.5% normal goat serum/PBS, pH 7.40, followed by incubation with primary antibodies at optimal dilution at room temperature for 30 min (monoclonal antibodies) or at +4° C. for 15 hours (polyclonal antibodies). The primary antibodies were diluted with a 0.1% bovine serum albumin/PBS solution. After washing in PBS, endogenous peroxidase activity was blocked with 10-min incubation with 0.1% hydrogen peroxidase (30%)/PBS solution. With intervening washes in PBS, the specimens were further incubated with biotinylated antibodies in the PBS buffer at RT for 30 min; detected with avidin-biotinylated horseradish complex in the PBS buffer at RT for 30 min and the reaction was revealed by AEC (Vector Laboratories). The slides were counterstained with Mayer's haemalum. To determine the density of positive cells, four random fields of each quadrant of the cross section were counted with 40× magnification, and the score is given as a total for 1 mm². Antibodies and dilutions used were CD8+

T cells (5 mg/mL, 22071D) from BD Pharmingen, San Diego, CA and KIM-1 (8 mg/mL, AF3689) from R&D systems, Abingdon, UK.

Hyaluronan (HA) was stained from paraffin sections using a specific biotinylated bHABC hyaluronan binding complex, which contains biotinylated G1 domain of aggrecan and link protein, prepared from bovine articular cartilage, by avidin-biotin-peroxidase detection (Vector Laboratories; 1:200 dilution) with 0.05%±3,3-diaminobenzidine (DAB) (Sigma Chemical Co., St. Louis, MO), as described. The specificity of the staining was controlled by digesting some sections with *Streptomyces* hyaluronidase in the presence of protease inhibitors before staining, or pre-incubating the bHABP probe with hyaluronan oligosaccharides. Ten photographs with 40× magnification were taken from each sample and the area positive for hyaluronan was measured with computer-assisted imagining (Zeiss Axionvision 4.4, Carl Zeiss International). The average area of these 10 measurements was used in statistical analyses. All analyses were performed in a blinded manner by two independent observers.

Renal histology. Semi-quantitative assessment of histologic damage was carried out as follows: 2 mm thick paraffin-embedded kidney samples were stained with hematoxylin and eosin. The severity of following parameters of tubular injury (flattening, dilatation, casts and necrosis) was graded on a scale from 0 to 3 as follows: grade 0=no damage, grade 1=mild damage, grade 2=moderate damage, grade 3=severe damage, and represented as overall tubular injury score (0-12).

Statistics. All data are mean+/−SEM and analyzed by SPSS for Windows, version 15.0 (SPSS Inc, Chicago, IL). For two-group comparison, non-parametric Mann-Whitney U test and parametric Student's t-test were applied. For multiple-group comparison, non-parametric Kruskal-Wallis test with the Dunn post hoc test and parametric ANOVA with Dunnett's cor-rection were applied. For survival, Kaplan-Meier analysis with log rank (Mantel-Cox) was applied. $P<0.05$ was regarded as statistically significant.

Results

Thrombin Time

Figure 1:
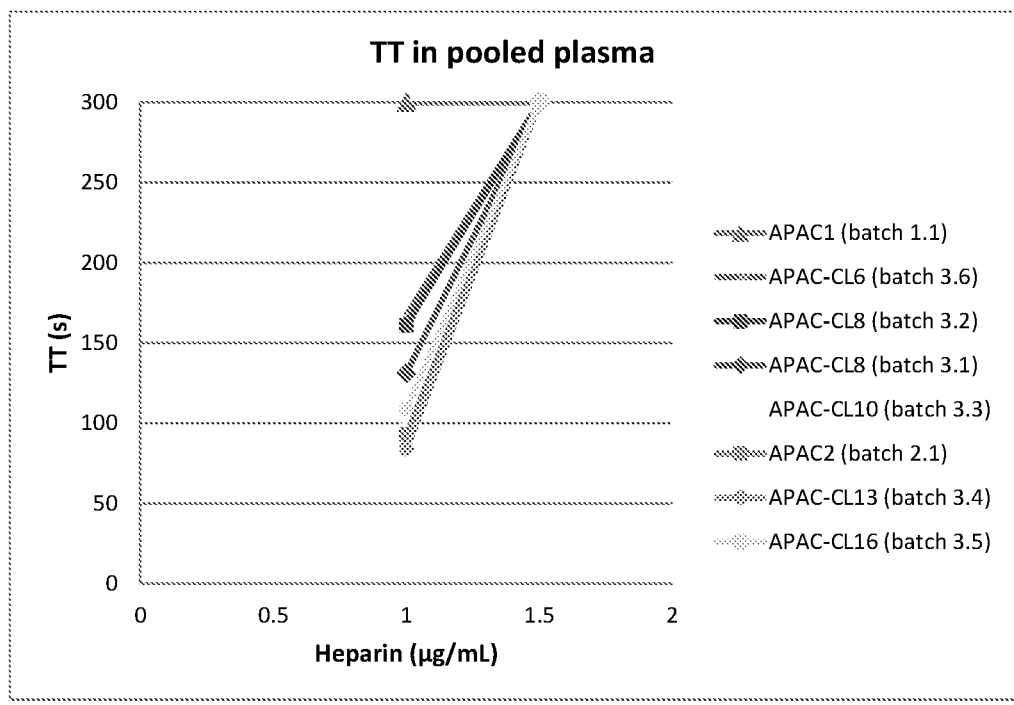
FIG. 1. Shows screening of the effect on thrombin time (TT) in the presence of two concentrations of the first generation APAC1 (batch 1.1, 4 Hep chains), the second generation APAC2 (batch 2.1, 11 Hep chains) and the third generation APAC-CL6 to CL16 (batch: 3.1; 3.2; 3.3; 3.4; 3.5 and 3.6, 8; 8; 10; 13; 16 and 6 Hep chains, respectively) at heparin (Hep) [C] of 1.0 and 1.75 µg/mL in pooled plasma. TT baseline was 28 s.
Figure 2:
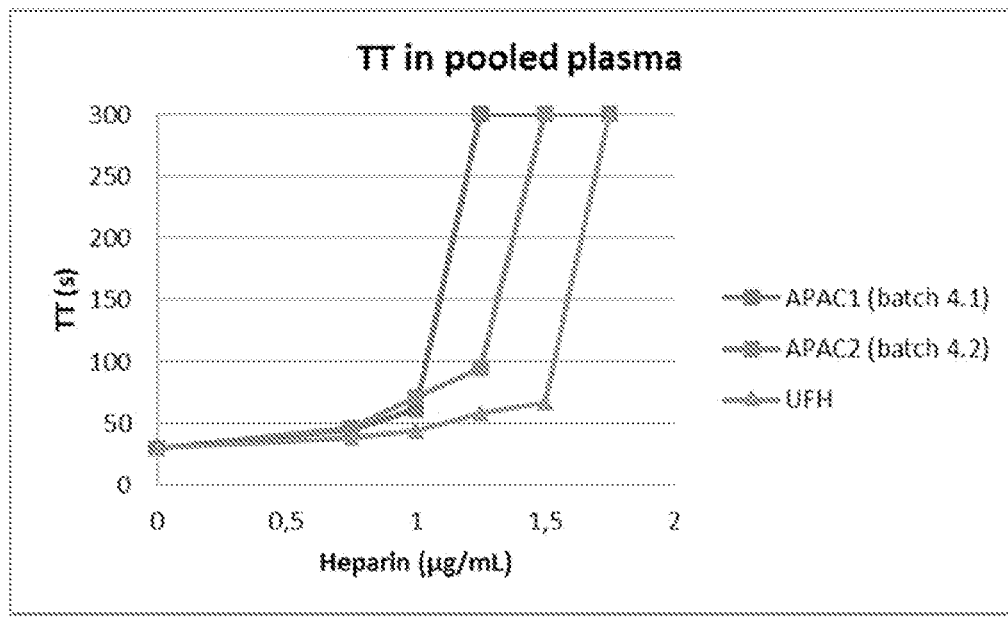
FIG. 2. Shows thrombin time (TT) in the presence of three to five concentrations of the fourth generation APAC1 (batch 4.1, 4 Hep chains) and APAC2 (batch 4.2, 8 Hep chains) at Hep [C] of 0.75; 1.0 and 1.75 µg/mL in pooled plasma. TT baseline was 31 s.

An example of the TT measurement in pooled plasma in the presence of APAC complexes (CL 6:1 to 16:1) from 2010 to 2012 is shown in FIG. 1, and for APAC1 (batch 4.1) and APAC2 (batch 4.2) in FIG. 2.

FIG. 1

At 1 µg/mL, all APACs prolonged TT at least by 1.5-fold, while UFH prolonged the TT by 1.3-fold the baseline (30 s). APAC1 (batch 1.1, 4 Hep chains) reached the max TT (300 s) measured, while APAC2 (batch 2.1, 11 Hep chains) prolonged TT 2.5-fold the baseline (FIG. 1). APAC-CL6 (6 Hep chains) prolonged TT 5.5-fold, APAC-CL8, batch 3.2 (8 Hep chains), 5.8-fold and batch 3.1 (8 Hep chains) 4.3-fold, APAC-CL10 (10 Hep chains) 2.4-fold, APAC-CL13 (13 Hep chains) 2.5-fold and APAC-CL16 (16 Hep chains) 3.7-fold the baseline value (FIG. 1). At 1.5 µg/mL all APACs and UFH reached the max time of the measurement.

FIG. 2

APAC1 (batch 4.1, 4 Hep chains) and APAC2 (batch 4.2, 8 Hep chains) prolonged TT 2.1- to 2.4-fold, respectively (FIG. 2). At 1.25 µg/mL APAC1 (batch 4.1, 4 Hep chains) reached the max time (300 s) measured, while APAC2 (batch 4.2, 8 Hep chains) prolonged TT 3.2-fold (FIG. 2).

Activated Partial Thromboplastin Time

FIG. 3

Figure 3:
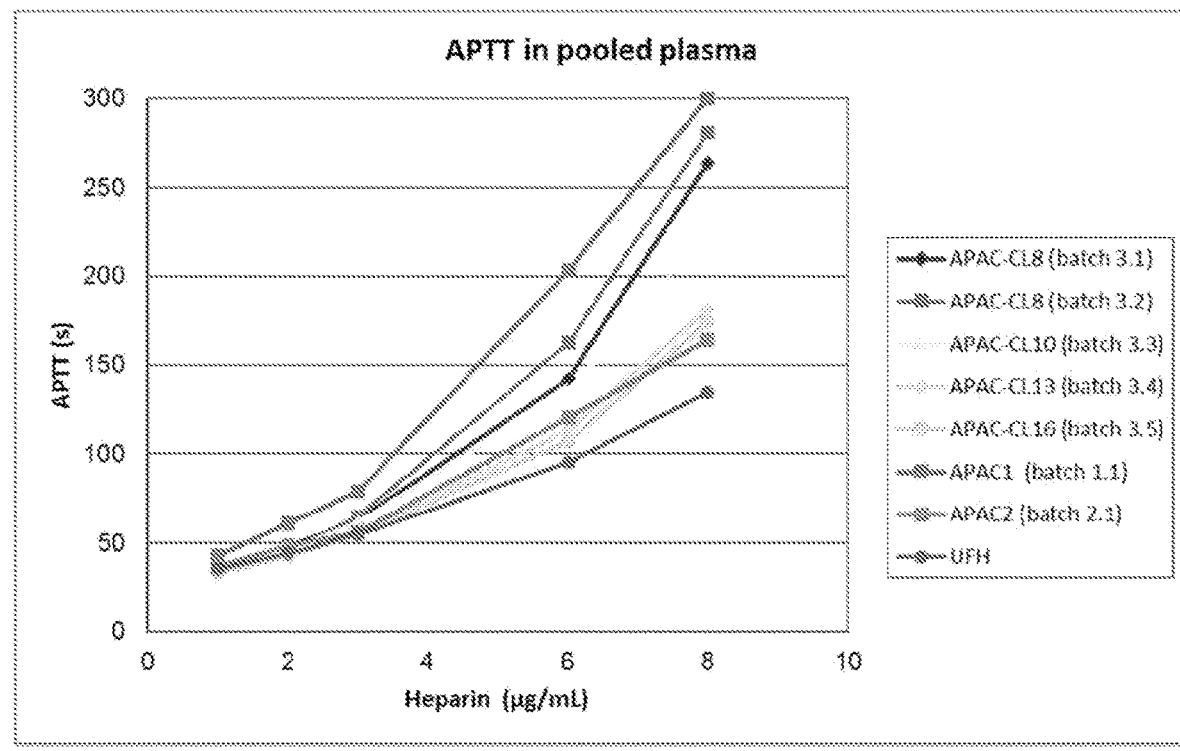
FIG. 3. Shows activated partial thromboplastin time (APTT) in the presence of five concentrations of the first generation APAC1 (batch 1.1, 4 Hep chains), the second generation APAC2 (batch 2.1, 11 Hep chains) and the third generation APAC-CL8 to -16 (batches 3.1; 3.2; 3.3; 3.4 and 3.5, 8, 8, 10, 13 and 16 Hep chains, respectively) at Hep [C] 1;2;3;6 and 8 µg/mL in pooled plasma. APTT baseline was 30 s.

An example of the APTT measurement in pooled plasma in the presence of APAC1 (batch 1.1, 4 Hep chains), APAC2 (batch 2.1, 11 Hep chains) and APACs with CL 6:1 to 16:1 from batches 3.1 to 3.5 (8, 8, 10, 13, 16 Hep chains) is shown in FIG. 3.

In comparison to the APTT baseline (30 s), at 1 µg/mL, APAC1 (batch 1.1) prolonged APTT 1.4-fold, while the other APACs and UFH prolonged the APTT 1.1 to 1.2-fold. At 2 µg/mL APAC1 (batch 1.1) prolonged APTT 2.0-fold, while the other APACs and UFH exhibited less, 1.4- to 1.6-fold prolongation. At 3 µg/mL in comparison with the baseline APAC1 (batch 1.1, 4 Hep chains) prolonged the APTT 2.6-fold, APAC-CL8 (batch 3.1 and 3.2, 8 Hep chains) 2.1-fold, APAC-CL10 (batch 3.3, 10 Hep chains) 2.0-fold, APAC2 (batch 2.1, 11 Hep chains) 1.9-fold, APAC-CL13 (batch 3.4, 13 Hep chains), APAC-CL16 (batch 3.5, 16 Hep chains) and UFH all 1.8-fold. At 6 µg/mL APAC1 (batch 1.1, 4 Hep chains) prolonged APTT 6.7-fold, APAC-CL8 (batches 3.1 and 3.2, 8 Hep chains) 5.4- to 4.7-fold, APAC-CL10 (batch 3.3, 10 Hep chains) 4.5-fold, APAC2 (batch 2.1, 11 Hep chains) 4-fold, APAC-CL13 (batch 3.4, 13 hep chains) 3.8-fold, APAC-CL16 (batch 3.5, 16 hep chains) 3.6-fold and UFH 3.1-fold. At 8 µg/mL APAC1 (batch 1.1, 4 Hep chains) prolonged APTT 9.8-fold, APAC-CL8 (batch 3.1 and 3.2, 8 hep chains) 9.3- to 8.7-fold, APAC-CL10 (batch 3.3, 10 Hep chains) 7.4-fold, APAC-CL13 (batch 3.4, 13 hep chains) 6.0-fold, APAC2 (batch 2.1, 11 Hep chains) 5.4-fold, APAC-CL16 (batch 3.5. 16 Hep chains) 5.8-fold and UFH 4.2-fold, the least. At the highest concentration used the difference in APTT between APAC1 (batch 1.1, 4 Hep chains) and APAC-CL10 (batch 3.3, 10 Hep chains) was 25% and between APAC2 (batch 2.1, 11 Hep chains) 45%. In all, APTT was typically most prolonged in comparison with baseline in the presence of the lowest CLs of the first and the second generation APACs (batch 1.1 and 2.1, 4 and 11 Hep chains).

The fourth generation of APACs (APAC1 versus APAC2) differed from the previous batches in that APTT prolongation was quite similar, until a higher (above 6 µg/mL) dose of Hep was used. Then again, the anticoagulation benefitted from the lower coupling CL of heparin. At 1 µg/mL, APAC1 (batch 4.1, 4 Hep chains) and APAC2 (batch 4.2, 8 Hep chains) both prolonged APTT 1.2-fold in comparison with the baseline value (29 s). At 2 µg/mL APAC1 (batch 4.1) and APAC2 (batch 4.2) prolonged APTT similarly, 1.4- and 1.3-fold, respectively. At 3 µg/mL again APAC1 (batch 4.1) and APAC2 (batch 4.2) prolonged APTT similarly 1.8- and 1.7-fold, respectively. At 6 µg/mL APAC1 (batch 4.1) and APAC2 (batch 4.2) prolonged APTT 3.9- and 3.4-fold, respectively. At 8 µg/mL APAC1 (batch 4.1) and APAC2 (batch 4.2) prolonged APTT 7.5- and 6.0-fold, respectively. At the highest concentration used, the difference in APTT between APAC1 (batch 4.1) and APAC-2 (batch 4.2) was 21%.

FIG. 4

Figure 4:
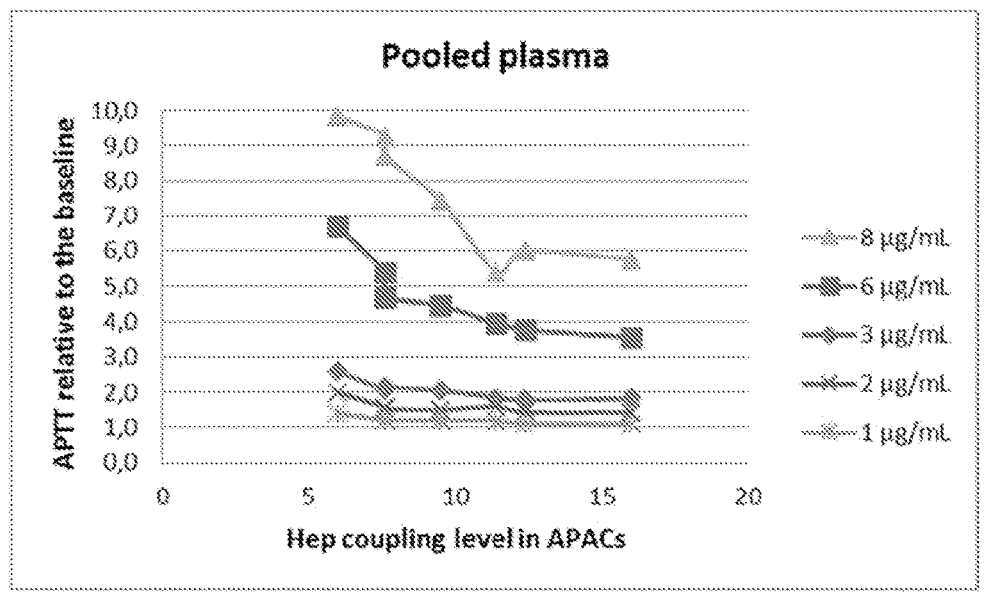
FIG. 4. Shows a comparison of heparin conjugation level in APACs at five different heparin concentrations on the prolongation (1- to 10-fold) of APTT. Results with APAC1 (batch 1.1, 4 Hep chains), APAC-CL8 (batches 3.1 and 3.2, 8 Hep chains), APAC-CL10 (batch 3.3, 10 Hep chains), APAC2 (batch 2.1, 11 Hep chains), APAC-CL13 (batch 3.4, 13 Hep chains), APAC-CL16 (batch 3.5, 16 Hep chains) on APTT at Hep [C] 1; 2; 3; 6; 8 µg/mL are shown in pooled plasma. APTT baseline was 30 s.

The APTT-assessed anticoagulant action of APACs with different heparin couplings, CLs is shown in FIG. 4.

FIG. 5

Figure 5:
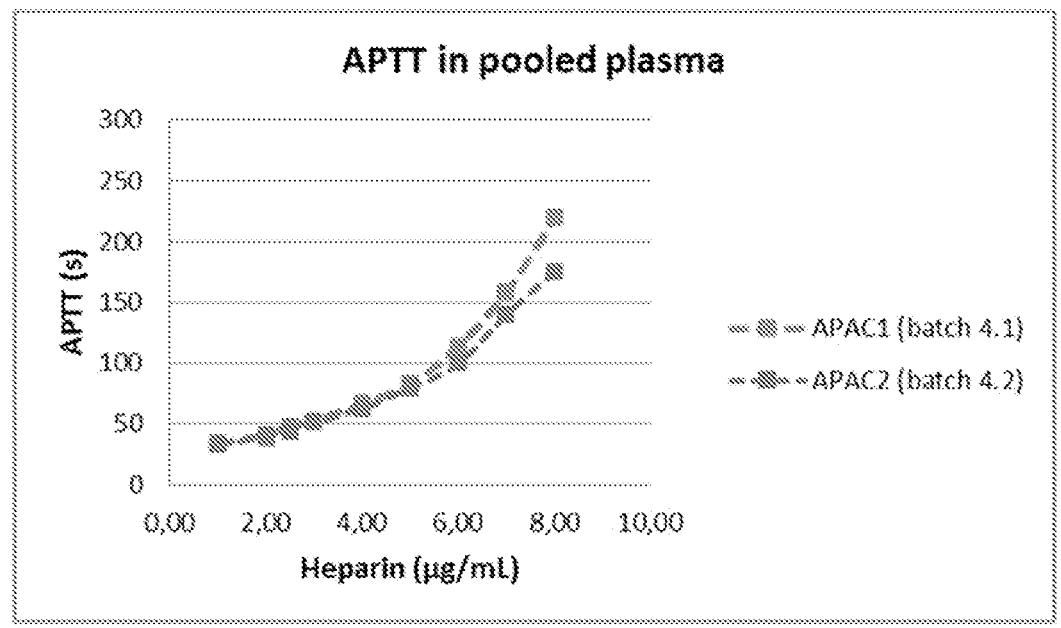
FIG. 5. Shows APTT in the presence of five concentrations of the fourth generation APAC1 (batch 4.1, 4 Hep chains) and APAC2 (batch 4.2, 8 hep chains) at Hep [C] 1; 2; 3; 6 and 8 µg/mL in pooled plasma. APTT baseline was 30 s.
Figure 6A:
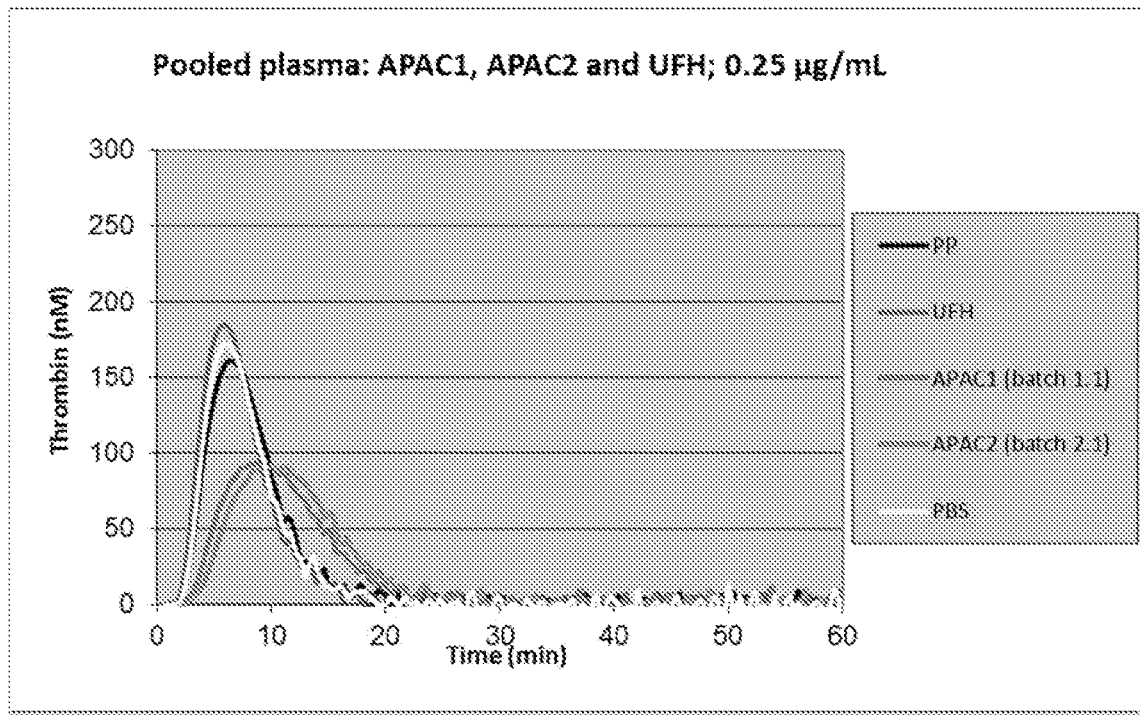
FIG. 6A. Shows delayed thrombin generation by Calibrated Automated Thrombograms in the presence of 0.25 µg/mL of the first generation APAC1 (batch 1.1, 4 Hep chains), the second generation APAC2 (batch 2.1, 11 Hep chains), in comparison with UFH and phosphate buffered saline (PBS) in pooled plasma (PP) supplemented with 5 pM tissue factor (TF) and 4 µM phospholipids (PPL).
Figure 6B:
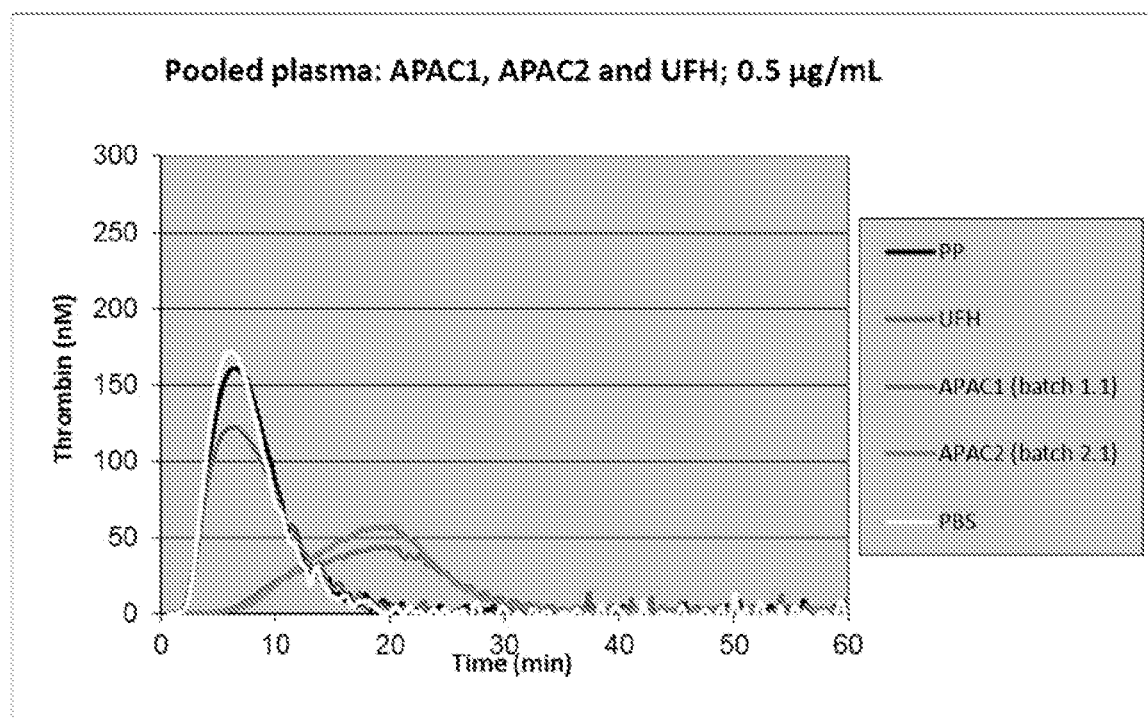
FIG. 6B. Shows delayed thrombin generation by Calibrated Automated Thrombograms in the presence of 0.5 µg/mL of the first generation APAC1 (batch 1.1, 4 Hep chains), the second generation APAC2 (batch 2.1, 11 Hep chains), in comparison with UFH and phosphate buffered saline (PBS) in pooled plasma (PP) supplemented with 5 pM tissue factor (TF) and 4 µM phospholipids (PPL).
Figure 7A:
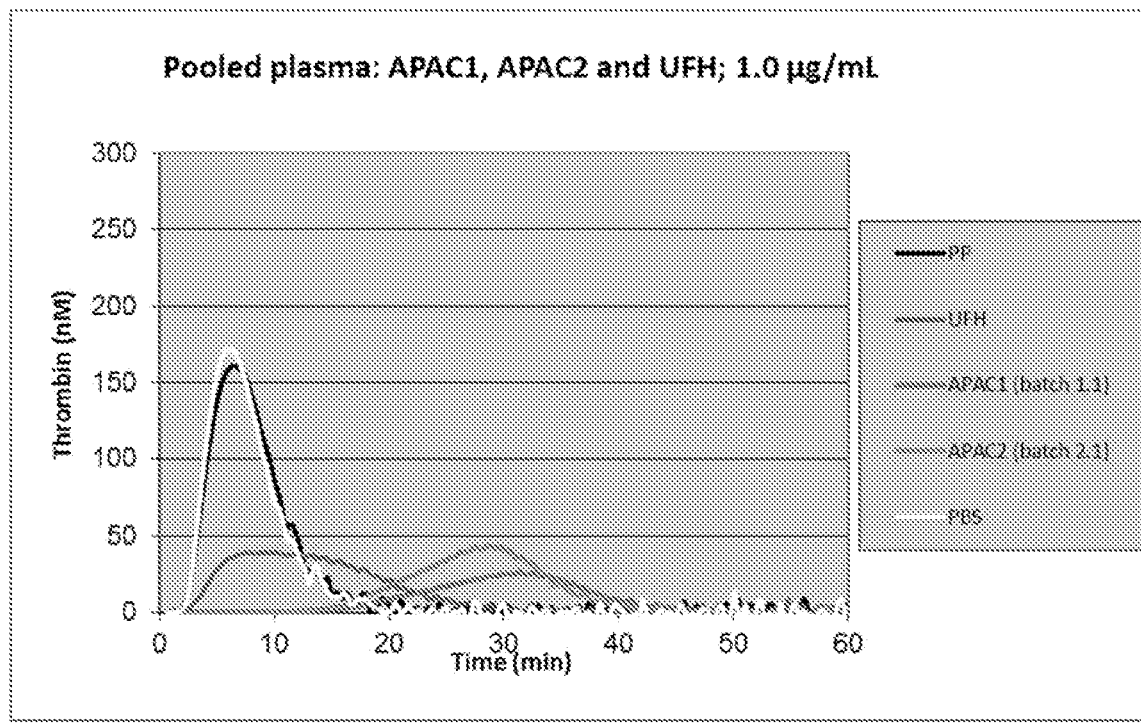
FIG. 7A. Shows delayed thrombin generation by Calibrated Automated Thrombograms in the presence of 1.0 µg/mL of the first generation APAC1 (batch 1.1, 4 Hep chains), the second generation APAC2 (batch 2.1, 11 Hep chains), in comparison with UFH and PBS in pooled plasma (PP) supplemented with 5 pM TF and 4 µM PPL.
Figure 7B:
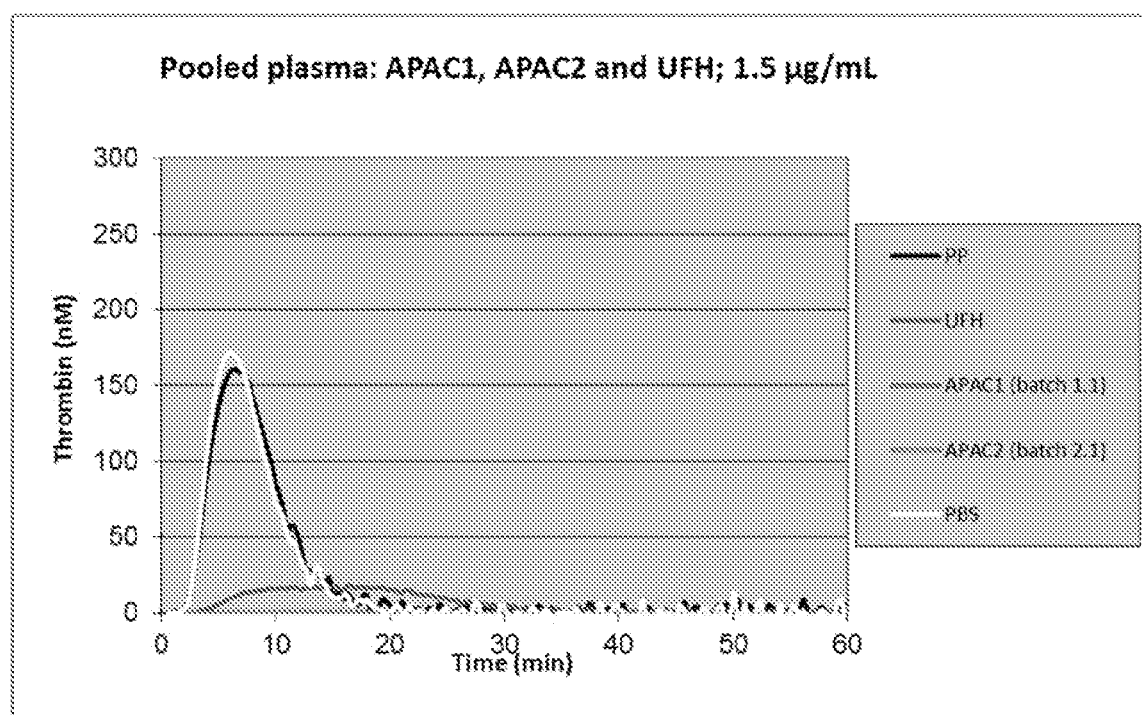
FIG. 7B. Shows delayed thrombin generation by Calibrated Automated Thrombograms in the presence of 1.5 µg/mL of the first generation APAC1 (batch 1.1, 4 Hep chains), the second generation APAC2 (batch 2.1, 11 Hep chains), in comparison with UFH and PBS in pooled plasma (PP) supplemented with 5 pM TF and 4 µM PPL.
Figure 8A:
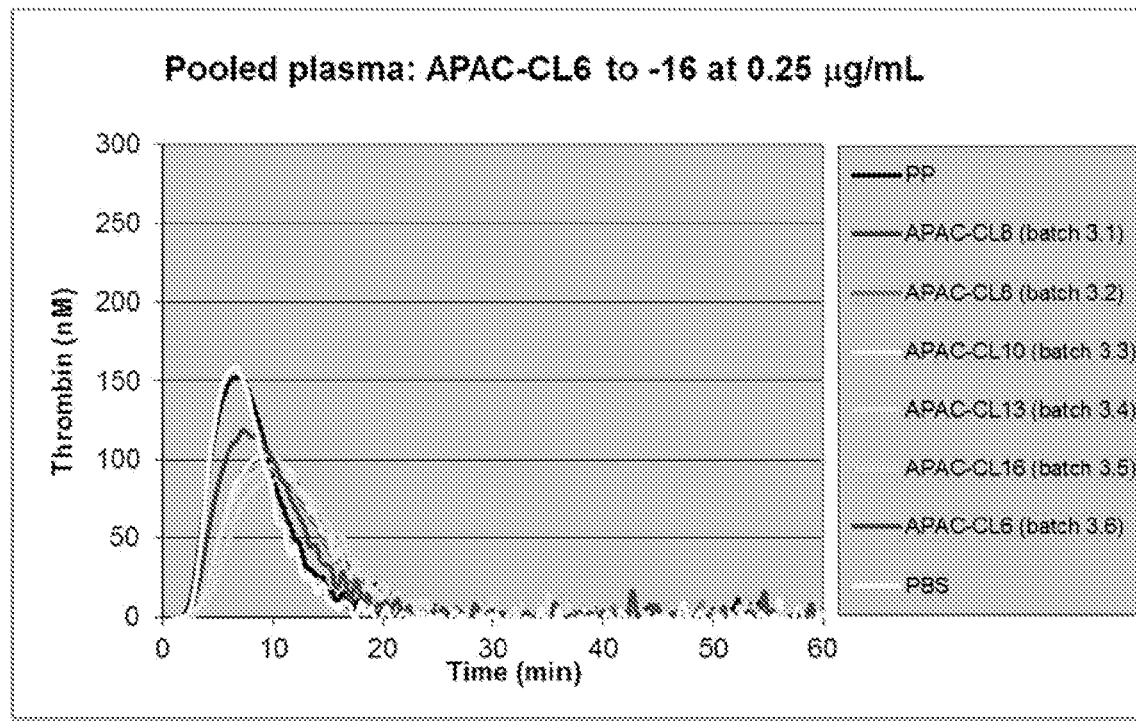
FIG. 8A. Shows thrombin generation by Calibrated Automated Thrombogram in the presence of 0.25 µg/mL of the third generation APAC-CL6 to -CL16 (8, 8, 10, 13, 16 and 6 Hep chains) and PBS in pooled plasma (PP) supplemented with 5 M TF and 4 µM PPL. APAC-CL8 (batch 3.1 and 3.2, 8 Hep chains), APAC-CL10 (batch 3.3, 10 Hep chains), APAC-CL13 (batch 3.4, 13 Hep chains), APAC-CL16 (batch 3.5, 16 Hep chains) and APAC-CL6 (batch 3.6, 6 Hep chains).
Figure 8B:
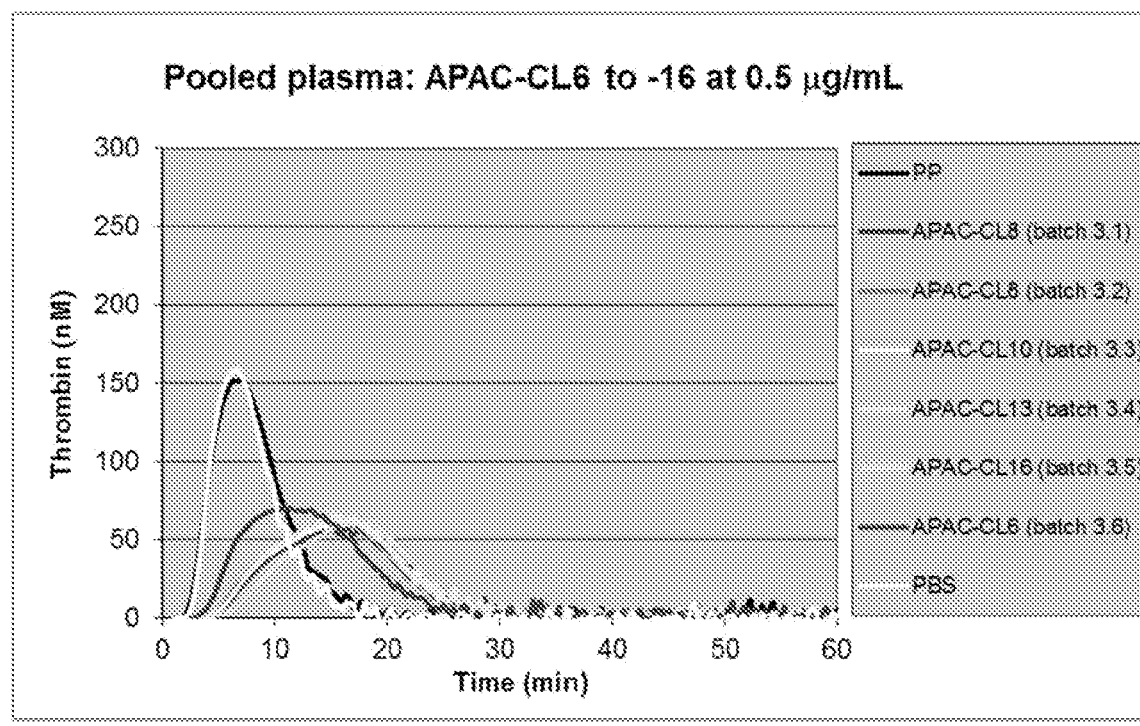
FIG. 8B. Shows thrombin generation by Calibrated Automated Thrombogram in the presence of 0.5 µg/mL of the third generation APAC-CL6 to -CL16 (8, 8, 10, 13, 16 and 6 Hep chains) and PBS in pooled plasma (PP) supplemented with 5 M TF and 4 µM PPL. APAC-CL8 (batch 3.1 and 3.2, 8 Hep chains), APAC-CL10 (batch 3.3, 10 Hep chains), APAC-CL13 (batch 3.4, 13 Hep chains), APAC-CL16 (batch 3.5, 16 Hep chains) and APAC-CL6 (batch 3.6, 6 Hep chains).
Figure 9A:
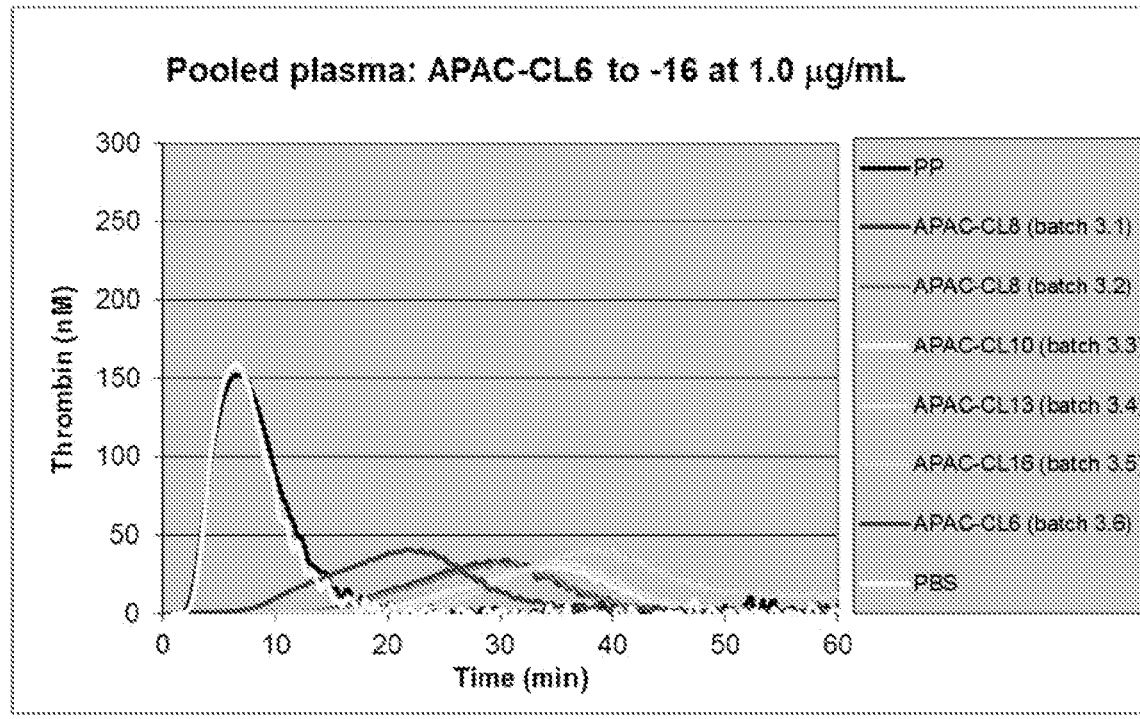
FIG. 9A. Shows thrombin generation by Calibrated Automated Thrombogram in the presence of 1.0 µg/mL of APAC-CL6 to -CL16 (8, 8, 10, 13, 16 and 6 Hep chains) and PBS in pooled plasma (PP) supplemented with 5 M TF and 4 µM PPL. APAC-CL8 (batch 3.1 and 3.2, 8 Hep chains), APAC-CL10 (batch 3.3, 10 Hep chains), APAC-CL13 (batch 3.4, 13 Hep chains), APAC-CL16 (batch 3.5, 16 Hep chains) and APAC-CL6 (batch 3.6, 6 Hep chains).
Figure 9:
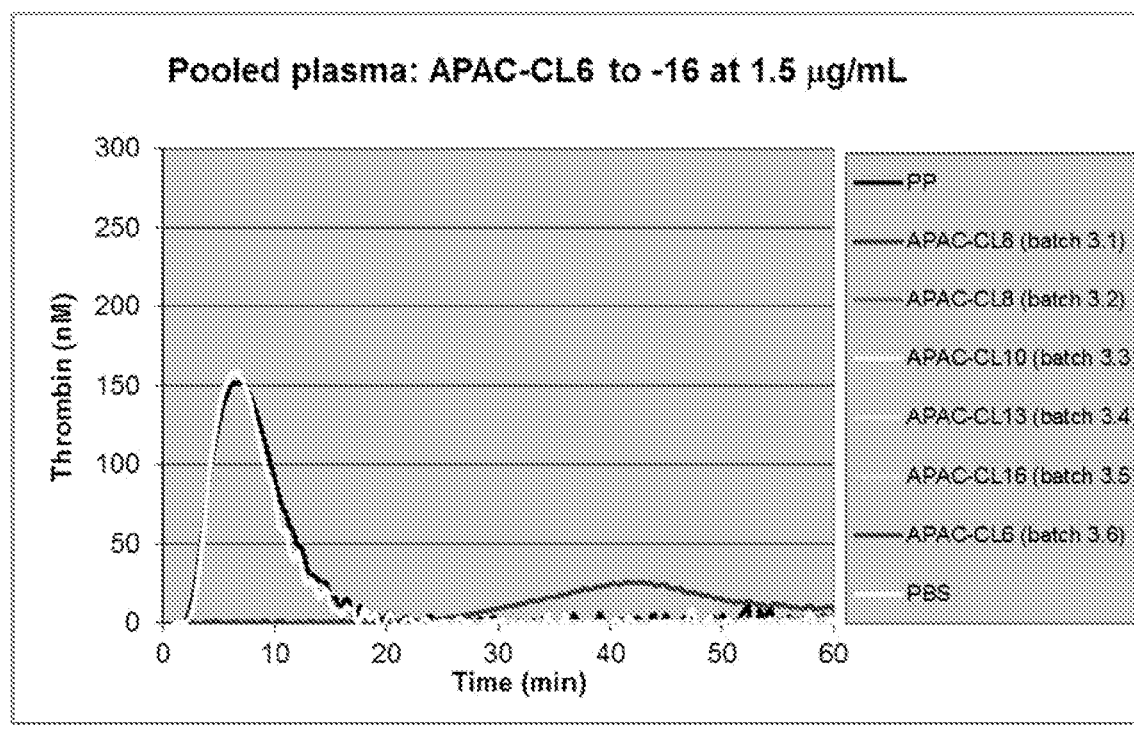
FIG. 9B. Shows thrombin generation by Calibrated Automated Thrombogram in the presence of 1.5 µg/mL of APAC-CL6 to -CL16 (8, 8, 10, 13, 16 and 6 Hep chains) and PBS in pooled plasma (PP) supplemented with 5 M TF and 4 µM PPL. APAC-CL8 (batch 3.1 and 3.2, 8 Hep chains), APAC-CL10 (batch 3.3, 10 Hep chains), APAC-CL13 (batch 3.4, 13 Hep chains), APAC-CL16 (batch 3.5, 16 Hep chains) and APAC-CL6 (batch 3.6, 6 Hep chains).

APTT in the presence of the fourth generation APAC1 (batch 4.1, 4 Hep chains) and APAC2 (batch 4.2, 8 Hep chains) is shown in FIG. 5.

Calibrated Automated Thrombogram (CAT) in PPP

FIG. 6-9

CAT, which is triggered by tissue factor (5 pM), the extrinsic pathway activator, showed anticoagulant action with APACs at lower concentrations than needed to prolong APTT. At low heparin concentration of 0.25-1.5 µg/mL APACs reduced the peak and ETP and prolonged the ttpeak dose-dependently in all three different plasmas tested (PP, SHP and Octaplas). Thrombograms depicting the influence of the first generation APAC1 (batch 1.1, 4 Hep chains), the second generation APAC2 (batch 2.1, 11 Hep chains), UFH and the third generation APAC-CL6 to -16 in pooled plasma are shown as examples in FIG. 7-12 Lag time (s), ETP (nM), peak (nM), and ttpeak (s) for APAC1 (batch 1.1, 4 Hep chains) and APAC2 (batch 2.1, 11 Hep chains) are summarized in Table II and for APAC-CL6 to APAC-CL16 in Table III. The relative change (%) of the values in comparison with the vehicle control is shown. If thrombin generation was completely inhibited, lag time (s), ETP (nM), Peak (nM), ttPeak (s) is expressed as 0.

In comparison with UFH the lag time and ttpeak were clearly prolonged by all APACs at all concentrations tested. The ETP was reduced by APACs in comparison to UFH at all concentrations except for APAC-CL6 (batch 3.6, 6 Hep chains) at 1.0 µg/mL where ETP was similar to UFH. The peak was reduced by APACs in comparison to UFH at all concentrations, except for APAC2 (batch 2.1, 11 Hep chains) at 1.0 µg/mL where the peak value was similar to UFH. Thrombin generation was completely abolished with APACs at 1.5 µg/mL, except for APAC-CL6 (batch 3.6, 6 Hep chains), which exhibited 15% of the baseline peak value. Overall, APAC1 (batch 1.1, 4 Hep chains) and APAC2 (batch 2.1, 11 Hep chains) possessed relatively similar inhibition of thrombin generation. In the third generation APACs with CL 13:1 and 16:1 were more potent inhibitors than APACs with CL<10.

Calibrated Automated Thrombogram in PRP

FIGS. 10-12

These figures investigate platelet-dependent thrombin generation, i.e. procoagulant activity (to estimate the risk of bleeding or thrombosis), and show APACs inhibit thrombin generation.

In the presence of platelets, low (1 pM) TF trigger was used, and thereby also the thrombin generation was less than in the plasma CAT with added PPL. At low Hep concentration of 0.25-1.5 µg/mL, APACs reduced the peak and ETP and prolonged the ttpeak dose-dependently in PRP of individual healthy donors tested.

Figure 10:
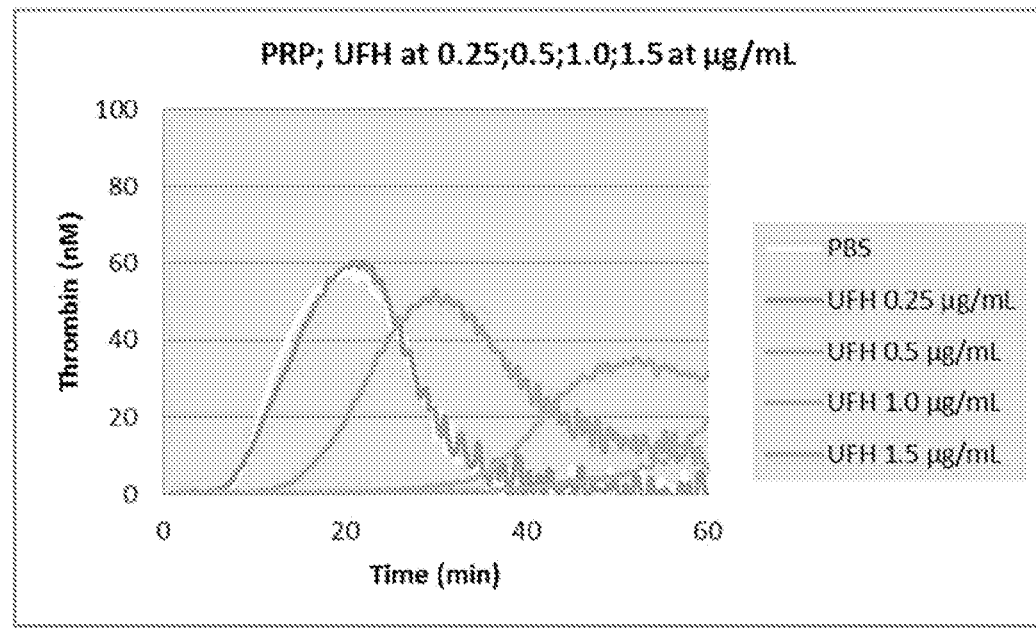
FIG. 10. Shows thrombin generation by Calibrated Automated Thrombograms in the presence of 0.25; 0.5; 1.0; and 1.5 µg/mL of UFH in platelet-rich plasma (PRP) supplemented with 1 pM TF platelets supplying the PPL.
Figure 11A:
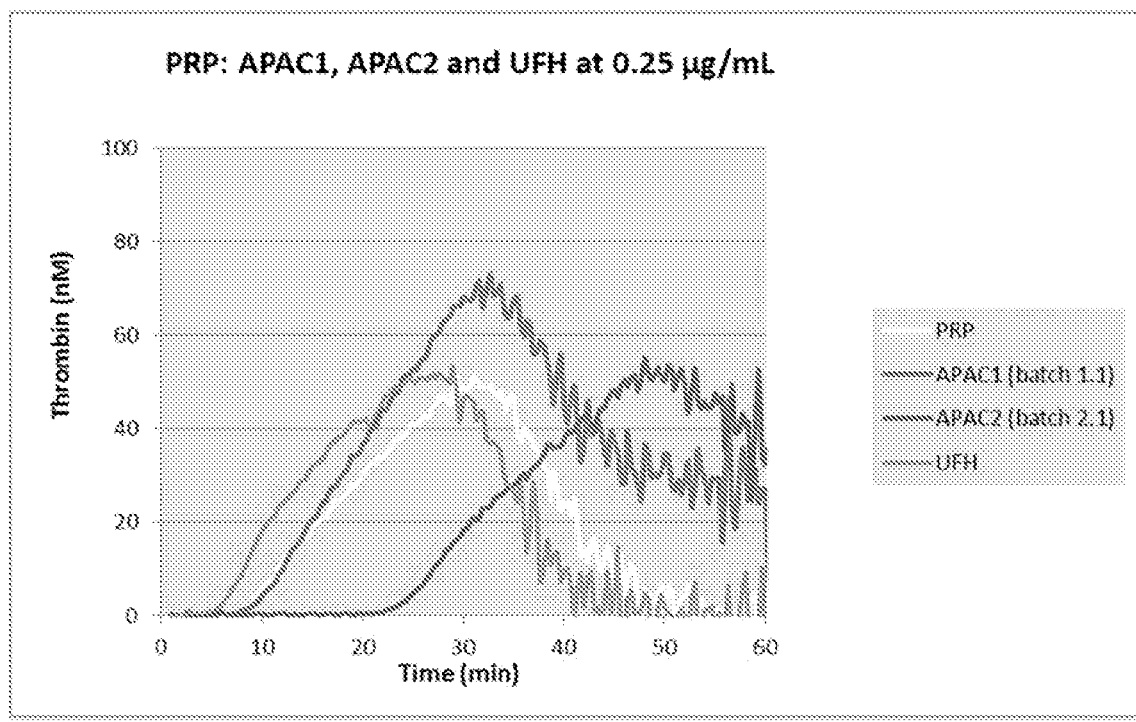
FIG. 11A. Shows thrombin generation by Calibrated Automated Thrombograms in the presence of 0.25 µg/mL of APAC1 (batch 1.1, 4 Hep chains) and APAC2 (batch 2.1, 11 Hep chains) and UFH in PRP (donor is a high responder) supplemented with 1 pM TF, platelets supplying the PPL.
Figure 11B:
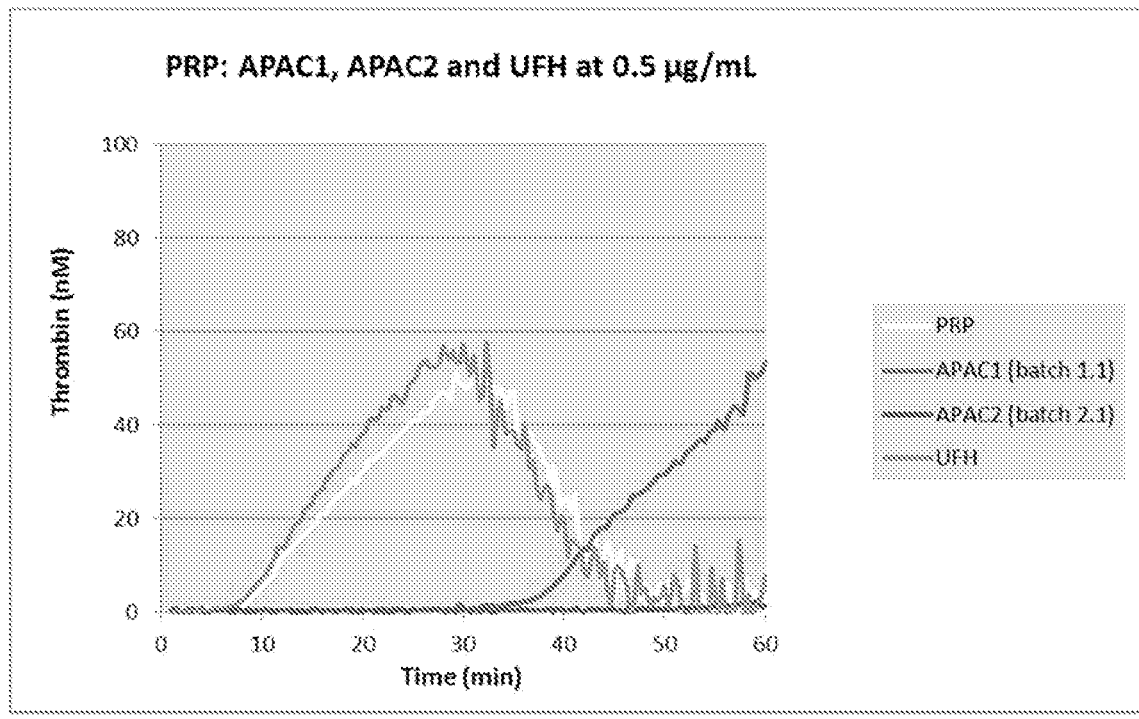
FIG. 11B. Shows thrombin generation by Calibrated Automated Thrombograms in the presence of 0.5 µg/mL of APAC1 (batch 1.1, 4 Hep chains) and APAC2 (batch 2.1, 11 Hep chains) and UFH in PRP (donor is a high responder) supplemented with 1 pM TF, platelets supplying the PPL.
Figure 12A:
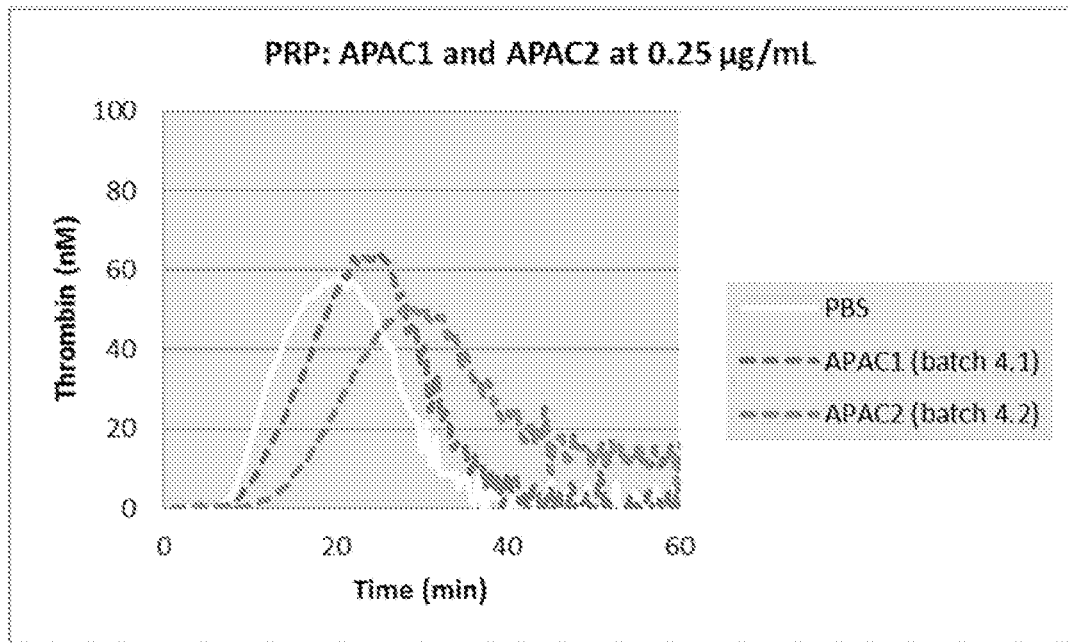
FIG. 12A. Shows thrombin generation by Calibrated Automated Thrombograms in the presence of 0.25 µg/mL of APAC1 (batch 4.1, 4 Hep chains) and APAC2 (batch 4.2, 8 Hep chains) and in PRP (donor is a moderate responder) supplemented with 1 pM TF, platelets supplying the PPL.
Figure 12B:
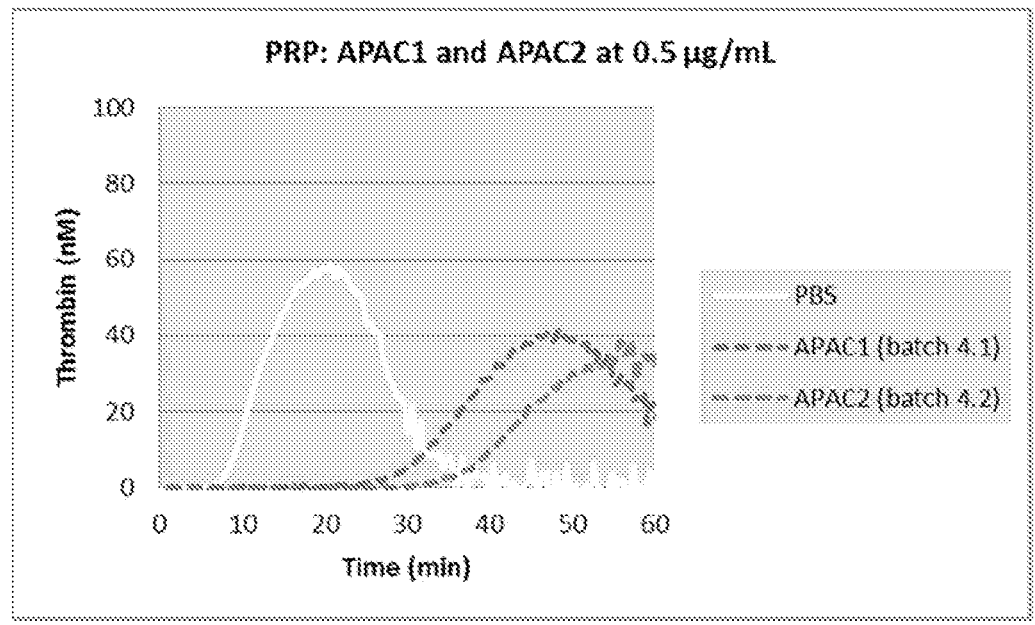
FIG. 12B. Shows thrombin generation by Calibrated Automated Thrombograms in the presence of 0.5 µg/mL of APAC1 (batch 4.1, 4 Hep chains) and APAC2 (batch 4.2, 8 Hep chains) and in PRP (donor is a moderate responder) supplemented with 1 pM TF, platelets supplying the PPL.
Figure 12C:
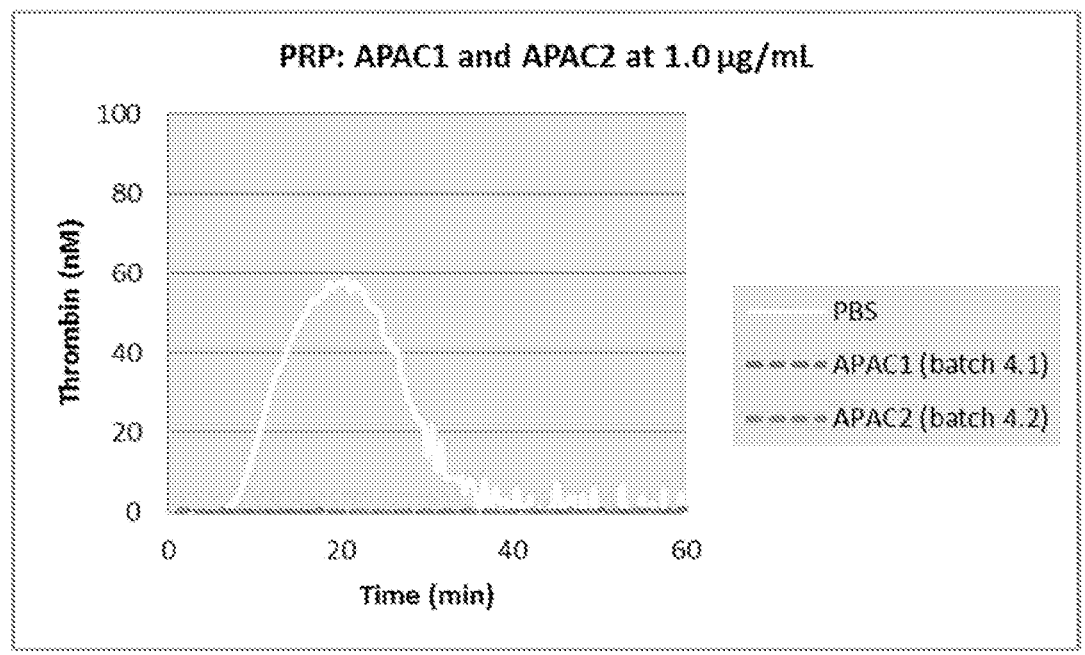
FIG. 12C. Shows thrombin generation by Calibrated Automated Thrombograms in the presence of 1.0 µg/mL of APAC1 (batch 4.1, 4 Hep chains) and APAC2 (batch 4.2, 8 Hep chains) and in PRP (donor is a moderate responder) supplemented with 1 pM TF, platelets supplying the PPL.

Thrombograms depicting the influence of UFH concentration in FIG. 10, the first generation APAC1 (batch 1.1, 4 Hep chains), the second generation APAC2 (batch 2.1, 11 Hep chains) in FIG. 11, and the fourth generation APAC1 (batch 4.1, 4 Hep chains) and APAC2 (batch 4.2, 8 Hep chains) in FIG. 12, are shown as examples using the selected concentrations reflecting the outcome of the studies. At 0.5 µg/mL APACs were at least twice as potent inhibitors of thrombin generation as UFH. APACs with CL 8:1 and 11:1 were stronger inhibitors of platelet-procoagulant activity and reduced the peak and the ttpeak more than APACs with CL 6:1. At 1.0 µg/mL the difference in the efficacy towards UFH was even more pronounced by all APACs.

In summary, thrombin generation was delayed and platelet activity was inhibited clearly with APACs in comparison with UFH. The higher the number of heparin chains conjugated the stronger was the inhibition.

Collagen-Induced Platelet Aggregation

Figure 13A:
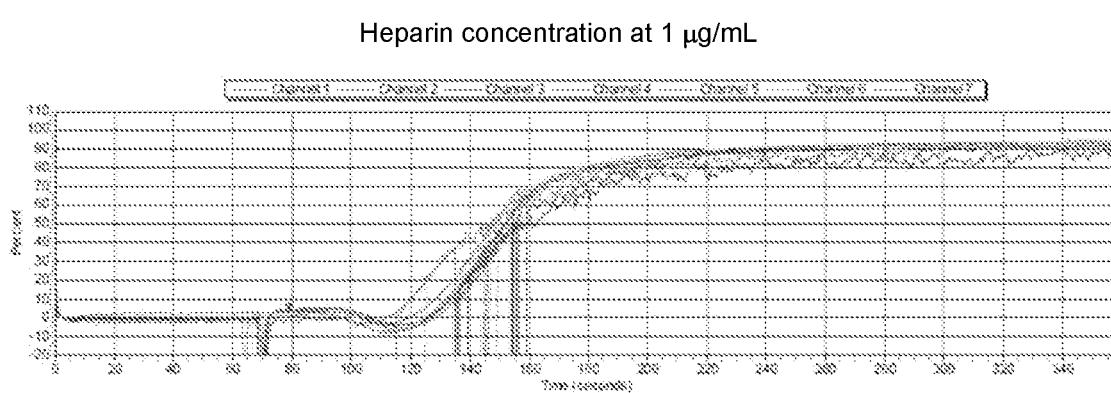
FIG. 13A. Shows collagen-induced aggregation in PRP in the presence of the third generation APACs, APAC-CL6 to -CL-16 (8, 8, 10, 13, 16 and 6 Hep chains). An example of the low responder to APACs at Hep [C] of 1 µg/mL is given. Channel 1: APAC-CL8 (batch 3.1, 8 Hep chains), channel 2: APAC-CL8 (batch 3.2, 8 Hep chains), channel 3: APAC-CL10 (batch 3.3, 10 Hep chains), channel 4: APAC-CL13 (batch 3.4, 13 Hep chains), channel 5: APAC-CL16 (batch 3.5, 16 Hep chains), channel 6: APAC-CL6 (batch 3.6, 6 Hep chains) and channel 7: mixture of APAC-CL10 and -16 (10 Hep chains and 16 Hep chains). The [C] of collagen was 0.5 µg/mL.
Figure 13B:
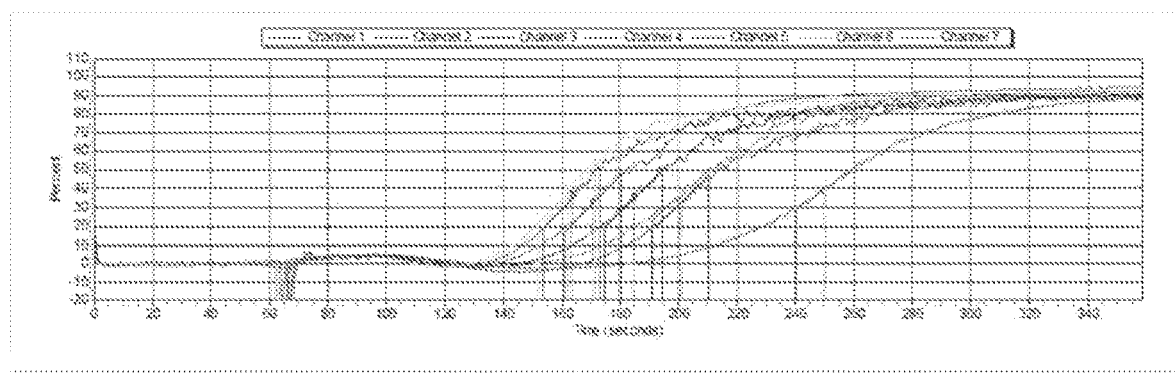
FIG. 13B. Shows collagen-induced aggregation in PRP in the presence of the third generation APACs, APAC-CL6 to -CL-16 (8, 8, 10, 13, 16 and 6 Hep chains). An example of the low responder to APACs at Hep [C] of 10 µg/mL is given. Channel 1: APAC-CL8 (batch 3.1, 8 Hep chains), channel 2: APAC-CL8 (batch 3.2, 8 Hep chains), channel 3: APAC-CL10 (batch 3.3, 10 Hep chains), channel 4: APAC- CL13 (batch 3.4, 13 Hep chains), channel 5: APAC-CL16 (batch 3.5, 16 Hep chains), channel 6: APAC-CL6 (batch 3.6, 6 Hep chains) and channel 7: mixture of APAC-CL10 and -16 (10 Hep chains and 16 Hep chains). The [C] of collagen was 0.5 µg/mL.
Figure 13C:
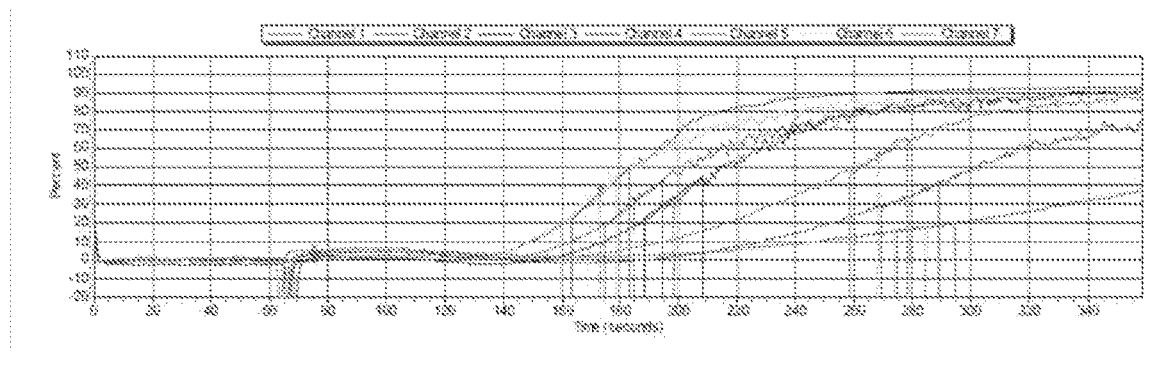
FIG. 13C. Shows collagen-induced aggregation in PRP in the presence of the third generation APACs, APAC-CL6 to -CL-16 (8, 8, 10, 13, 16 and 6 Hep chains). An example of the low responder to APACs at Hep [C] of 30 µg/mL is given. Channel 1: APAC-CL8 (batch 3.1, 8 Hep chains), channel 2: APAC-CL8 (batch 3.2, 8 Hep chains), channel 3: APAC-CL10 (batch 3.3, 10 Hep chains), channel 4: APAC-CL13 (batch 3.4, 13 Hep chains), channel 5: APAC-CL16 (batch 3.5, 16 Hep chains), channel 6: APAC-CL6 (batch 3.6, 6 Hep chains) and channel 7: mixture of APAC-CL10 and -16 (10 Hep chains and 16 Hep chains). The [C] of collagen was 0.5 µg/mL.
Figure 14:
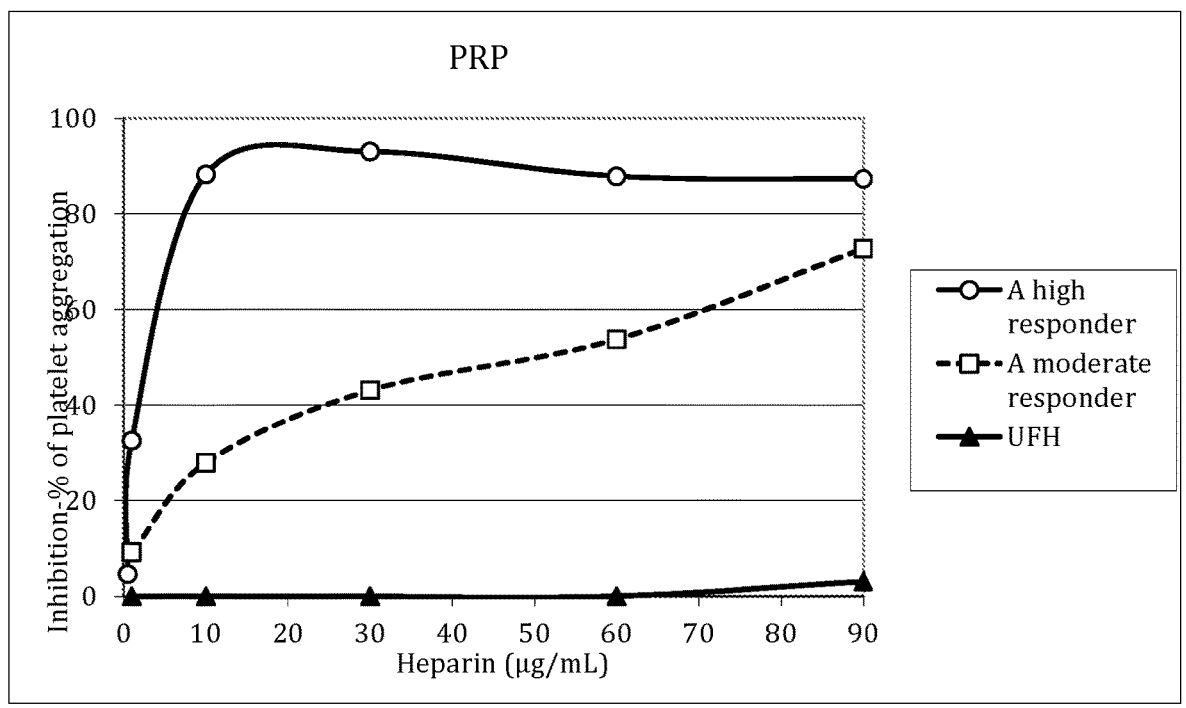
FIG. 14. Shows inhibition of collagen-induced maximal platelet aggregation in the presence of APAC1 (batch 1.1, 4 hep chains) in PRP with a representative high (open circle) and a moderate (open square) responder to APACs at 3; 10; 30; 60 and 90 µg/mL. The mean inhibition of platelet aggregation in donors in the presence of UFH (black triangle) is also shown. Inhibition of the maximal platelet aggregation relative to the vehicle (PBS) is shown as percentage (%).

FIGS. 13-14. Representative aggregation curves in donors having high (50% of donors), moderate (30% of donors) and low susceptibility to APACs (FIG. 13) and the pooled dose-response analysis of APAC1 in a high and moderate responder (FIG. 14).

FIG. 13. APACs APAC-CL6 to -CL16 (at Hep [C] 1; 3; 10; 30 and 90 µg/mL) were tested in citrate anticoagulated PRP from 3 independent donors, each with a different susceptibility (defined as inhibition % at heparin concentration of 30 µg/mL (overall ED50): high >60%, low <40% and moderate 40-60% responder to APACs in collagen (coll; 0.5 µg/mL)-induced platelet aggregation. Results on maximal aggregation-% and slope of the curve (speed of aggregation) at 6 min were detected.

APAC-CL6 to APAC-CL16 (8, 8, 10, 13, 16 and 6 Hep chains) and APAC1 (batch 1.1, 4 Hep chains) reduced the rate and maximal platelet aggregation, whereas UFH failed. APACs with higher coupling CL 11 to 16:1 were more potent inhibitors than molecules with lower CL 6 to 10:1. Results at 1, 10 and 30 µg/mL with the low responder are presented in FIG. 13 for APAC-CL6 to APAC-CL16. The aggregation curves (related to speed of aggregation) declined dose dependently with all APAC variants, although the maximal aggregation was less affected. APAC-CL16 (batch 3.5, 16 Hep chains) was the best inhibitor in this low responder (donor 2) and reduced the maximal aggregation-% from 92 to 38%.

FIG. 14. APAC1 (batch 1.1, 4 Hep chains) inhibited 90% of the maximal platelet aggregation at 10 µg/mL in a high responder PRP, while 90 µg/mL was required to inhibit 75% of the aggregation in a moderate responder PRP. Results at 3; 10; 30; 60 and 90 µg/mL of APAC1 with the high and moderate responders are presented.

Acute Models of Thrombosis in Baboons

FIGS. 15-16

Figure 15:
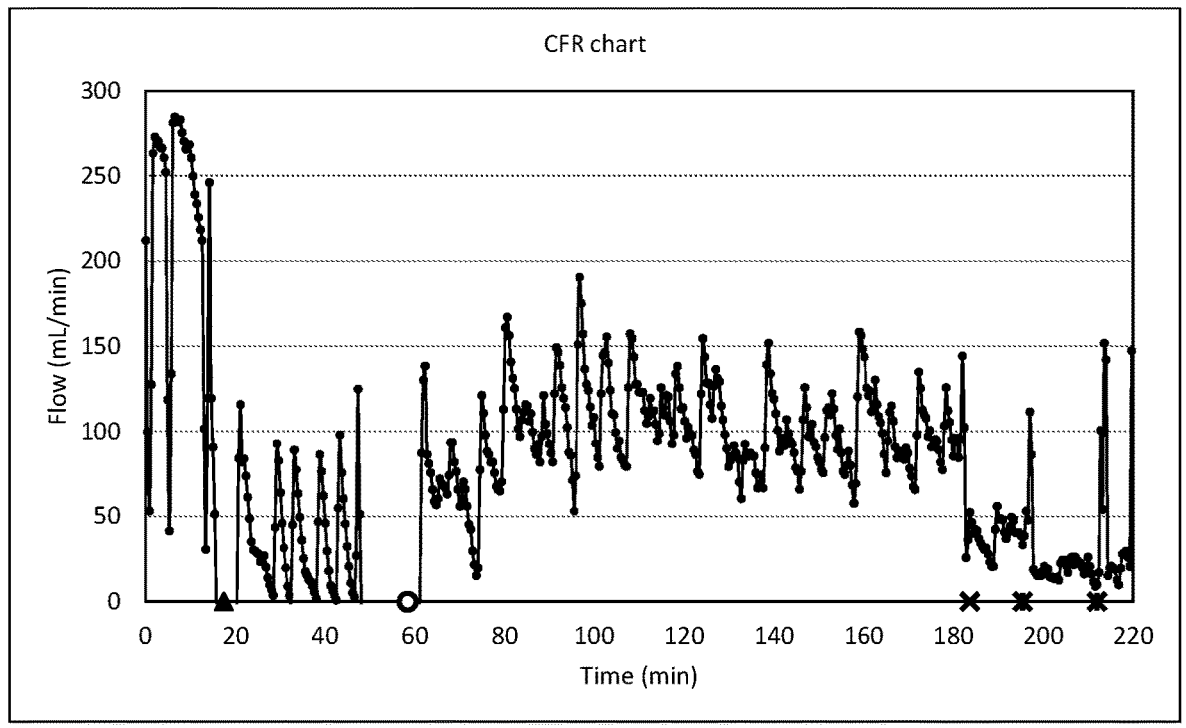
FIG. 15. Shows a chart of cyclic flow reductions (CFR) after the local application of UFH and APAC1 (batch 1.1, 4 Hep chains) (both at 4 mg/mL; 2 mg in total) on the fresh injury site in the modified Folt's model of acute thrombosis in baboons. Immediately after baseline blood flow returned, the artery was stenosed (30%) to the flow rate of 100 mL/min. Repeated occlusions (5 CFRs within 25 min) were observed at the injury site treated with UFH (black triangle). Prior to implementing again the stenosis (at 20-50 min) and increasing the stenosis (at 180 min) the treated injury site was flushed with phosphate buffered saline (PBS).

In the acute thrombosis model in baboons APAC and UFH were administered locally on the injury at 4 mg/mL (FIG. 15). In the presence UFH the artery repeatedly (5 CFRs/27 min) occluded at flow rate of 100 mL/min (stenosed to 30%). In contrast, APAC1 (batch 1.1, 4 Hep chains) effectively inhibited thrombus formation until the experiment was interrupted, after the follow up time of 120 min. At the end of the experiment, at time point 180 min, the artery was restenosed first to 50 mL/min (60% stenosis) and finally to 30 mL/min (90% stenosis) while APAC continued to inhibit the occlusion for the selected test periods (10 and 15 min, respectively). In the control experiments with UFH and phosphate buffered saline (PBS) repetitive CFRs ensued (results not shown). In the baboon thrombosis model on the extracorporeal collagen graft (FIG. 16), APAC1 reduced platelet deposition on collagen by 34±13% (mean and SD, n=4, p=0.01) in comparison with UFH. The distal thrombus propagation was also diminished by 63±11% (n=4, p=0.19). Results with UFH were similar to untreated control values (n=21). Fibrin accumulation was reduced by APAC1 (45±14%), but not by UFH (1.1±0.1%, n=4, p=0.01).

Compatible with the strong retention potential and slow degradation PET detected un-degraded APAC at the anastomotic sites in rats for over 50 h (−120 h), whereas UFH was undetectable already after 24 h (n=2). About 10% APAC attached directly to the vascular application site. Both APAC and UFH were cleared via urinary pathway.

Ischemia Reperfusion Injury and Acute Kidney Injury Model.

FIGS. 17-20

Notably whilst an ischemia reperfusion injury has been demonstrated in an acute kidney injury model, the therapeutics of the invention have use in relation to any other reperfusion injury and so could be used to prevent, ameliorate or treat other such injuries as exemplified by myocardial infarction or stroke or peripheral arterial occlusive disease or mesenterial ischemia.

Kidney function recovery from IRI was analyzed. The doses of 16 or 32 µg of APAC2 (batch 2.1, 11 Hep chains) were based on hematological analyses in the rat. A clinically relevant dose range of APAC2 and comparative clinical doses of UFH were based on previous animal models. The dose related to the anticoagulant efficacy of APAC2 and UFH was shown after intravenous (i.v.) injection at 10 min by APTT (FIG. 17), where UFH prolonged APTT 3-fold more than the APAC2 at highest dose (80 µg). SD rats were treated either with saline vehicle (i.v.) or APAC2 16 or 32 µg (i.v.) 10 min before the both renal arteries were clamped for 30 min. To estimate the kidney function after ischemia, rat serum and plasma were collected for 3 days after reperfusion. In APAC2 32 µg treated rats, serum creatinine (P<0.01, FIG. 18A) and urea nitrogen (P<0.01, FIG. 18B) levels were reduced, when compared with the vehicle-treated rats. ELISA analysis of neutrophil gelatinase-associated lipocalin (NGAL) serum levels, a biomarker of kidney injury, revealed that APAC2 32 µg pretreatment also reduced tubulointerstitial injury (**P<0.01, FIG. 18C).

APAC2 pretreatment decreased danger-associated innate immunity ligand hyaluronan expression and inflammatory cell infiltration in a 30-min bilateral renal artery clamping model.

The right kidneys were removed 3 days after reperfusion. The density of tubulointerstitial injury marker Kim-1 depicted that the number of injured immunoreactive tubuli was significantly reduced in the APAC2 32 µg-pretreated rat kidneys compared with those of vehicle treated (*P<0.05, FIG. 19B). As IRI induces renal cortical accumulation of an innate immunity ligand hyaluronan (HA), we analyzed the effect of APAC2 pretreatment on HA protein expression after IRI. In kidneys subjected to 30-min warm ischemia and 3 day reperfusion, APAC2 32 µg pretreatment significantly reduced the HA immunoreactive area, when compared with vehicle-treated kidneys (*P<0.05, FIG. 19A).

Semi-quantitative assessment of tubular injury comprising analysis of tubular dilatation, epithelial necrosis, flattening and casts revealed severe tubular injury in vehicle-treated kidneys at 3 days (FIG. 19). Both APAC2 16 and 32 µg pretreatment reduced total tubular injury score as only mild tubular dilatation and flattening of epithelium was observed in isolated tubular cross-sections (*P<0.05, FIG. 19).

APAC pretreatment prevents acute kidney injury in a one-hour bilateral renal artery clamping model.

Finally, we studied the effect of APAC (batch 2.1, 11 heparin chains) pretreatment in a severe, nearly irreversible IRI model. Both renal arteries were clamped for one hour. The SD rats received either saline vehicle (i.v.) or 32 µg (i.v.) 10 min before the induction of warm ischemia. Rat survival was 75% (6 of 8) in vehicle-treated and 100% (8 of 8) in APAC2 32 µg group (*P<0.05, FIG. 20 A).

Next, we analyzed renal function with serum creatinine and urea nitrogen measurements. APAC2 pretreatment reduced serum creatinine and urea nitrogen levels, when compared with vehicle-treated kidneys (red dashed-line, P<0.01 and *P<0.001, FIGS. 20 B & C).

Thrombin Time and Activated Partial Thromboplastin Time in Antithrombin-Depleted Plasma An example of the TT and APTT measurement in AT-depleted plasma in the presence of APAC1 (batch 5.1, 4 Hep chains) and APAC2 (batch 5.2, 8 Hep chains) are shown in FIG. 21. and 22, respectively. Heparin concentration is determined with heparin starting material as the standard.

FIG. 21

At 1 µg/mL, APAC1 (batch 5.1, 4 Hep chains) prolonged TT at least by 2-fold the baseline, and at 2 µg/mL TT reached the maximum time measured (250 s). At 2 µg/mL APAC2 (batch 5.2, 8 Hep chains) prolonged TT 4.6-fold the baseline (FIG. 21).

FIG. 22

At 4 µg/mL, all APAC1 (batch 5.1, 4 Hep chains) prolonged APTT by 1.4-fold the baseline, and at 5 µg/mL 1.7-fold. At 4 µg/mL APAC2 (batch 5.2, 8 Hep chains) prolonged APTT 1.9-fold the baseline (FIG. 22). At 4 µg/mL UFH prolonged the APTT by 1.5-fold the baseline.

Conclusions of the Conjugation Level (CL) of Hep and its Association with Anticoagulant and Antiplatelet Effects All variants express dual anticoagulant and antiplatelet (collagen-induced aggregation and platelet pro-coagulant activity) actions.

APACs with CL 6-16:1 Share the Following Anticoagulant Properties:

(Heparin concentration estimated on Blyscan GAG standard)

Prolongation of APTT similarly to UFH at clinical doses (about 3 µg/mL)

Prolongation of APTT more efficiently than UFH at high clinical doses (about 6-8 g/mL)

APACs with Hep CL 6:1 appear more potent anti-coagulants than APACs with CL≥8:1, especially at higher concentrations.

Thrombin generation in CAT was delayed and reduced both in PPP and PRP at lower concentrations than needed for APTT prolongation (1.0 µg/mL) at least as efficiently as UFH APACs with CL≥8:1 appear more potent in inhibiting thrombin generation in PRP than the species with lower CL APACs have Antiplatelet Properties:

Reduce the rate and maximal platelet aggregation induced by collagen in citrated PRP, while UFH fails APACs with CL (8-16:1) are uniformly more potent inhibitors of collagen-induced platelet aggregation than molecules with CL 4-6:1

APACs with

CL≤6:1 prolong TT more than APACs with CL≥8

CL≤6:1 prolong APTT more than APACs with CL≥8

CL≥8:1 inhibit thrombin generation in CAT especially in PRP more than APAC with CL 4-6:1

CL≥8:1 inhibit collagen-induced PRP aggregation more than APAC with CL 4-6:1

Overall, inhibition of both the platelet aggregation and platelet procoagulant activity are benefitting from the high number of heparin chains conjugated to HSA.

Table I. APACs and conjugation level of Hep to HSA.

Two different methods were used to analyse the Hep [C] for the determination of conjugation level (CL) to HSA i.e. mol Hep per mol HSA:

1. Heparin starting material (Hep st.); and
2. Glycosaminoglycan standard (GAG st.).

HSA [C] was measured with BCA assay.

| CL Hep st. BCA | CL GAG st. BCA | Identification | Nickname | Batch | Year | Manufacturer Solvias Gmbh, Switzerland |
|---|---|---|---|---|---|---|
| 4 | 8 | APAC1 | APL001 | 1.1 | 2010 | Report L09--1647-201-125 |
| 11 | 17 | APAC2 | APL00X Fraction A | 2.1 | 2011 | N11-02672-Report_20110623 |
| 8 | 12 | APAC-CL8 | CR1 | 3.1 | 2012 | N11-13045A_REP_01 |
| 8 | 11 | APAC-CL8 | CR2 | 3.2 | 2012 | N11-13045A_REP_01 |
| 10 | 14 | APAC-CL10 | CR3 | 3.3 | 2012 | N11-13045A_REP_01 |
| 13 | 20 | APAC-CL13 | CR4 | 3.4 | 2012 | N11-13045A_REP_01 |
| 16 | 26 | APAC-CL16 | CR5 | 3.5 | 2012 | N11-13045A_REP_01 |
| 6 | 8 | APAC-CL6 | CR6 | 3.6 | 2012 | N11-13045A_REP_01 |
| 4 | 7.5 | APAC1 | APL001 | 4.1 | 2013 | N11-1210326_REP_01 |

| CL Hep st. BCA | CL GAG st. BCA | Identification | Nickname | Batch | Year | Manufacturer Solvias Gmbh, Switzerland |
|---|---|---|---|---|---|---|
| 8 | 15 | APAC2 | APL00X | 4.2 | 2013 | N11-1210326_REP_01 |
| 4 | n.d. | APAC1 | APL001 | 5.1 | 2014 | N14-10639_REP_01 |
| 8 | n.d. | APAC2 | APL00X | 5.2 | 2014 | N14-10639_REP_01 |

TABLE II

Thrombin generation in CAT in the presence of the first generation APAC1 (batch 1.1), the second generation APAC2 (batch 2.1), UFH and PBS in pooled plasma (PP) triggered with 5 pM TF and 4 μM phospholipids (PPL). Hep concentration is estimated on Blyscan (GAG st.) in the assay.

| | Hep conc. μg/mL | Lag time | ETP | Peak | ttPeak | Change-% relative to vehicle control | | | |
|---|---|---|---|---|---|---|---|---|---|
| | | | | | | Lag time | ETP | Peak | ttPeak |
| PP | | 2.7 | 1144.5 | 160.8 | 6.7 | | | | |
| UFH | 0.25 | 2.3 | 1190 | 185.1 | 6.0 | −12.4 | 4.9 | 7.6 | −2.8 |
| APAC1 (batch 1.1) | 0.25 | 3.3 | 1001.5 | 92.7 | 8.8 | 25.2 | −11.7 | −46.1 | 43.3 |
| APAC2 (batch 2.1) | 0.25 | 4.2 | 1022 | 90.7 | 10.2 | 56.4 | −9.9 | −47.3 | 64.8 |
| UFH | 0.5 | 2.3 | 1000.5 | 122.4 | 6.3 | −12.4 | −11.8 | −28.9 | 2.6 |
| APAC1 (batch 1.1) | 0.5 | 7.0 | 691 | 42.7 | 19.0 | 163.2 | −39.1 | −75.2 | 208.3 |
| APAC2 (batch 2.1) | 0.5 | 8.3 | 775.5 | 56.8 | 18.9 | 213.5 | −31.6 | −67.0 | 205.7 |
| UFH | 1.0 | 3.0 | 650 | 39.1 | 8.8 | 12.4 | −42.7 | −77.3 | 43.3 |
| APAC1 (batch 1.1) | 1.0 | 17.5 | 427 | 25.5 | 31.4 | 558.6 | −62.3 | −85.2 | 408.6 |
| APAC2 (batch 2.1) | 1.0 | 17.0 | 601 | 42.7 | 28.4 | 539.8 | −47.0 | −75.2 | 359.8 |
| UFH | 1.5 | 3.8 | 343 | 17.0 | 15.7 | 44.0 | −69.8 | −90.1 | 154.1 |
| APAC1 (batch 1.1) | 1.5 | 34.6 | 0 | 0.8 | 49.1 | 1198.9 | — | −99.5 | 695.5 |
| APAC2 (batch 2.1) | 1.5 | 0.0 | 0 | 0.0 | 0.0 | — | — | — | — |
| PBS | 0 | 2.7 | 1134 | 172.1 | 6.2 | 0.0 | 0.0 | 0.0 | 0.0 |

TABLE III

Thrombin generation in CAT in the presence of APAC-CL6 to APAC-CL16 and PBS in pooled plasma (PP) triggered with 5 pM TF and 4 μM PPL. Hep concentration is estimated on Blyscan (GAG st).

| | Hep conc. μg/mL | Lag time | ETP | Peak | ttPeak | change-% relative to vehicle control | | | |
|---|---|---|---|---|---|---|---|---|---|
| | | | | | | Lag time | ETP | Peak | ttPeak |
| PP | | 2.7 | 1123.0 | 152.7 | 6.8 | | | | |
| APAC-CL8 (batch 3.1) | 0.25 | 3.5 | 1059.0 | 102.1 | 9.2 | 16.7 | 2.1 | −35.6 | 44.9 |
| APAC-CL8 (batch 3.2) | 0.25 | 3.5 | 973.5 | 94.7 | 9.0 | 16.7 | −6.2 | −40.3 | 42.2 |
| APAC-CL10 (batch 3.3) | 0.25 | 3.5 | 1049.5 | 103.1 | 9.2 | 16.7 | 1.2 | −35.0 | 44.9 |
| APAC-CL13 (batch 3.4) | 0.25 | 3.8 | 1018.0 | 95.7 | 9.8 | 27.7 | −1.9 | −39.7 | 55.3 |
| APAC-CL16 (batch 3.5) | 0.25 | 4.2 | 995.5 | 88.3 | 10.2 | 39.0 | −4.0 | −44.3 | 60.7 |
| APAC-CL6 (batch 3.6) | 0.25 | 3.2 | 1064.5 | 117.8 | 7.8 | 5.7 | 2.6 | −25.8 | 23.7 |
| APAC-CL8 (batch 3.1) | 0.5 | 5.5 | 819.0 | 55.9 | 15.8 | 83.3 | −21.1 | −64.8 | 150.1 |

TABLE III-continued

Thrombin generation in CAT in the presence of APAC-CL6 to APAC-CL16 and PBS in pooled plasma (PP) triggered with 5 pM TF and 4 μM PPL. Hep concentration is estimated on Blyscan (GAG st ).

| | Hep conc. μg/mL | Lag time | ETP | Peak | ttPeak | change-% relative to vehicle control | | | |
|---|---|---|---|---|---|---|---|---|---|
| | | | | | | Lag time | ETP | Peak | ttPeak |
| APAC-CL8 (batch 3.2) | 0.5 | 5.3 | 829.0 | 59.7 | 15.5 | 77.7 | −20.1 | −62.4 | 144.9 |
| APAC-CL10 (batch 3.3) | 0.5 | 5.5 | 871.5 | 61.4 | 15.8 | 83.3 | −16.0 | −61.3 | 150.1 |
| APAC-CL13 (batch 3.4) | 0.5 | 5.7 | 892.5 | 64.3 | 15.7 | 89.0 | −14.0 | −59.5 | 147.6 |
| APAC-CL16 (batch 3.5) | 0.5 | 6.8 | 826.5 | 60.9 | 16.8 | 127.7 | −20.3 | −61.6 | 165.9 |
| APAC-CL6 (batch 3.6) | 0.5 | 4.2 | 928.5 | 70.0 | 11.2 | 39.0 | −10.5 | −55.9 | 76.5 |
| APAC-CL8 (batch 3.1) | 1.0 | 16.2 | 527.0 | 33.2 | 29.0 | 439.0 | −49.2 | −79.1 | 358.1 |
| APAC-CL8 (batch 3.2) | 1.0 | 16.3 | 514.0 | 31.3 | 29.8 | 444.3 | −50.5 | −80.3 | 371.2 |
| APAC-CL10 (batch 3.3) | 1.0 | 20.8 | 473.5 | 29.2 | 34.0 | 594.3 | −54.4 | −81.6 | 437.1 |
| APAC-CL13 (batch 3.4) | 1.0 | 22.2 | 507.5 | 32.1 | 34.8 | 639.0 | −51.1 | −79.8 | 450.2 |
| APAC-CL16 (batch 3.5) | 1.0 | 25.3 | 0.0 | 40.0 | 38.3 | 744.3 | −100.0 | −74.8 | 505.5 |
| APAC-CL6 (batch 3.6) | 1.0 | 9.2 | 648.5 | 39.9 | 22.0 | 205.7 | −37.5 | −74.8 | 247.6 |
| APAC-CL8 (batch 3.1) | 1.5 | 19.5 | 0.0 | 0.4 | 31.5 | 550.0 | — | −99.7 | 397.6 |
| APAC-CL8 (batch 3.2) | 1.5 | 48.3 | 0.0 | 3.7 | 58.2 | 1511.0 | — | −97.7 | 819.0 |
| APAC-CL10 (batch 3.3) | 1.5 | 49.5 | 0.0 | 1.5 | 56.8 | 1550.0 | — | −99.0 | 797.8 |
| APAC-CL13 (batch 3.4) | 1.5 | 21.5 | 0.0 | 0.5 | 25.7 | 616.7 | — | −99.7 | 305.5 |
| APAC-CL16 (batch 3.5) | 1.5 | 0.0 | 0.0 | 0.0 | 0.0 | — | — | — | — |
| APAC-CL6 (batch 3.6) | 1.5 | 26.3 | 0.0 | 25.3 | 42.0 | 777.7 | — | −84.1 | 563.5 |
| PBS | 0 | 3.0 | 1037.5 | 158.6 | 6.3 | 0 | 0 | 0 | 0 |

The invention claimed is:

1. A method for the manufacture of a medicament comprising an anti-thrombotic molecule having enhanced anti-platelet activity comprising:
   i) modifying an unfractionated heparin (Hep) chain to produce a reactant product having a sulfhydryl (-SH) group;
   ii) modifying a human serum albumin to produce a reactant product having a pyridyl dithiol (-PDP) group;
   iii) conjugating the reactant product of i) with the reactant product of ii) using a heterobifunctional cross-linker; and
   iv) repeating steps iii) and one or both of steps i) and ii) until the number of said heparin chains conjugated to said human serum albumin consists of an integer selected from the group of integers consisting of: 8, 9, 10, 11, 12, 13, 14, 15, and 16 wherein the heparin conjugated human serum albumin has enhanced anti-platelet activity.

2. The method according to claim 1, including providing said heterobifunctional cross-linker at a 1:1 stoichiometric ratio with said unfractionated Hep chain.

3. The method according to claim 1, wherein said heterobifunctional cross-linker is 3-(2-Pyridyldithio) propionic acid N-hydroxysuccinimide ester SPDP linker.

4. The method according to claim 1, wherein said anti-thrombotic molecule is purified by hydrophobic interaction chromatography (HIC) or ultra/diafiltration.

5. The method according to claim 1, including providing said unfractionated Hep chain of mammalian origin.

6. The method according to claim 5, including providing said unfractionated Hep chain of human, porcine, or bovine origin.

* * * * *

UNITED STATES PATENT AND TRADEMARK OFFICE
CERTIFICATE OF CORRECTION

PATENT NO. : 12,208,132 B2
APPLICATION NO. : 17/855932
DATED : January 28, 2025
INVENTOR(S) : Riitta Lassila Page 1 of 1

It is certified that error appears in the above-identified patent and that said Letters Patent is hereby corrected as shown below:

On the Title Page

Under item (*) Notice: Lines 4-5:
The statement "This patent is subject to a terminal disclaimer" is removed from the Notice section.

Signed and Sealed this
Twentieth Day of May, 2025

Coke Morgan Stewart
*Acting Director of the United States Patent and Trademark Office*